US010308588B2

(12) United States Patent
Córdova et al.

(10) Patent No.: US 10,308,588 B2
(45) Date of Patent: Jun. 4, 2019

(54) SYNTHESIS OF AMIDES AND AMINES FROM ALDEHYDES OR KETONES BY HETEROGENEOUS METAL CATALYSIS

(71) Applicant: ORGANOFUEL SWEDEN AB, Sundsvall (SE)

(72) Inventors: Armando Córdova, Stockholm (SE); Carlos Palo-Nieto, Bristol (GB); Samson Afewerki, Uppsala (SE)

(73) Assignee: ORGANOFUEL SWEDEN AB, Sundsvall (SE)

( * ) Notice: Subject to any disclaimer, the term of this patent is extended or adjusted under 35 U.S.C. 154(b) by 0 days.

(21) Appl. No.: 15/536,295

(22) PCT Filed: Dec. 15, 2015

(86) PCT No.: PCT/EP2015/079869
§ 371 (c)(1),
(2) Date: Jun. 15, 2017

(87) PCT Pub. No.: WO2016/096905
PCT Pub. Date: Jun. 23, 2016

(65) Prior Publication Data
US 2017/0362162 A1    Dec. 21, 2017

Related U.S. Application Data

(60) Provisional application No. 62/091,912, filed on Dec. 15, 2014.

(51) Int. Cl.
| C07D 307/34 | (2006.01) |
| C07C 209/28 | (2006.01) |
| C07D 317/58 | (2006.01) |
| C07C 41/18  | (2006.01) |
| C07C 41/26  | (2006.01) |
| C07C 45/38  | (2006.01) |
| C07C 213/02 | (2006.01) |
| C07C 227/08 | (2006.01) |
| C07C 231/02 | (2006.01) |
| C07D 307/52 | (2006.01) |
| B01J 23/44  | (2006.01) |
| B01J 31/02  | (2006.01) |
| B01J 35/00  | (2006.01) |
| B01J 35/04  | (2006.01) |

(52) U.S. Cl.
CPC ............ C07C 209/28 (2013.01); B01J 23/44 (2013.01); B01J 31/0238 (2013.01); B01J 35/0006 (2013.01); B01J 35/0013 (2013.01); B01J 35/04 (2013.01); C07C 41/18 (2013.01); C07C 41/26 (2013.01); C07C 45/38 (2013.01); C07C 213/02 (2013.01); C07C 227/08 (2013.01); C07C 231/02 (2013.01); C07D 307/52 (2013.01); C07D 317/58 (2013.01); B01J 2231/44 (2013.01); B01J 2531/005 (2013.01); C07B 2200/07 (2013.01); C07C 2601/14 (2017.05); C07C 2602/10 (2017.05)

(58) Field of Classification Search
CPC ......... C07C 41/18; C07C 41/26; C07C 45/38; C07B 2200/07
USPC ................................................. 549/440, 429
See application file for complete search history.

(56) References Cited

FOREIGN PATENT DOCUMENTS

| JP | H05310653 A     | 11/1993 |
| JP | H11206396 A     | 8/1999  |
| JP | 2004537588 A    | 12/2004 |
| WO | WO-2012/028721 A1 | 3/2012 |
| WO | WO-2015/144902 A1 | 10/2015 |

OTHER PUBLICATIONS

Abiraj et al, Zinc/ammonium formate: a new facile system for the rapid and selective reduction of oximes to amines, J. Chem. Research (S), 2003, p. 332-334. (Year: 2003).*
Mattias Anderson et al., "Total Synthesis of Capsaicin Analogues from Lignin-Derived Compounds by Combined Heterogeneous Meta, Organocatalytic and Enzymatic Cascades in One Pot," Advanced Synthesis & Catalysis, Jun. 2014, pp. 2113-2118, vol. 356, No. 9.
Mattias Anderson et al., "Total synthesis of capsaicin analogues from lignin-derived compounds by combined heterogeneous metal, organocatalytic and enzymatic cascades in one pot," Advanced Synthesis & Catalysis—Supporting Information, Apr. 2014, pp. 1-39, XP055248747.
Nandanan Erathodiyil et al., "Palladium Nanoclusters Supported on Propylurea-Modified Siliceous Mesocellular Foam for Coupling and Hydrogenation Reactions," Chemistry—A European Journal, Mar. 2008, pp. 3118-3125, vol. 14, No. 1, XP055037995.
B. Sreedhar et al., "Direct One-Pot Reductive Amination of Aldehydes with Nitroarenes in a Domino Fashion: Catalysis by Gum-Acacia-Stabilized Palladium Nanoparticles," The Journal of Organic Chemistry, Nov. 2009, pp. 8806-8809, vol. 74, No. 22, XP055248790.

(Continued)

Primary Examiner — Taylor V Oh
(74) Attorney, Agent, or Firm — Whitmyer IP Group LLC

(57) ABSTRACT

A mild and efficient synthesis of primary amines and amides from aldehydes or ketones using a heterogeneous metal catalyst and amine donor is disclosed. The initial heterogeneous metal-catalyzed reaction between the carbonyl and the amine donor components is followed by the addition of a suitable acylating agent component in one-pot, thus providing a catalytic one-pot three-component synthesis of amides. Integration of enzyme catalysis allows for eco-friendly one-pot co-catalytic synthesis of amides from aldehyde and ketone substrates, respectively. The process can be applied to asymmetric synthesis or to the co-catalytic one-pot three-component synthesis of capsaicin and its analogues from vanillin or vanillyl alcohol. A co-catalytic reductive amination/dynamic kinetic resolution (dkr) relay sequence for the asymmetric synthesis of optically active amides from ketones is disclosed. Implementation of a catalytic reductive amination/kinetic resolution (kr) relay sequence produces the corresponding optically active amide product and optical active primary amine product with the opposite stereochemistry from the starting ketones.

19 Claims, No Drawings

(56) References Cited

OTHER PUBLICATIONS

Marcelo E. Domine et al., "Development of metal nanoparticles supported materials as efficient catalysts for reductive amination reactions using high-throughput experimentation," Catalysis Today, available online Sep. 2010, pp. 2-11, vol. 159, No. 1, XP028134617.

Silvia Gomez et al., "The Reductive Amination of Aldehydes and Ketones and the Hydrogenation of Nitriles: Mechanistic Aspects and Selectivity Control," Advanced Synthesis & Catalysis, Wiley-VCH Verlag GmbH, Jan. 2002, pp. 1037-1057, vol. 344, No. 10, XP002420447.

Rafael Cano et al., "Impregnated palladium on magnetite as catalyst for multicomponent reductive amination reactions and other related reducing processes," Tetrahedron, Aug. 2011, pp. 8079-8085, vol. 67, No. 42, XP028294027, Elsevier Science Publishers, Amsterdam, NL.

Marcelo E. Domine et al., "Pt and Pd nanoparticles supported on structured materials as catalysts for the selective reductive amination of carbonyl compounds," Catalysis Today, May 2011, pp. 13-20, vol. 172, No. 1, XP028275030, Elsevier, NL.

Peter M. Gannett et al., "The Capsaicinoids: Their Separation, Synthesis, and Mutagenicity," The Journal of Organic Chemistry, Jan. 1988, pp. 1064-1071, vol. 53, No. 5, XP002200586, American Chemical Society, U.S.

Ryu Nakao et al., "Hydrogenation and Dehalogenation under Aqueous Conditions with an Amphiphilic-Polymer-Supported Nanopalladium Catalyst," Organic Letters, Jan. 2005, pp. 163-165, vol. 7, No. 1, XP055248784.

European Office Action Application No. 15 816 429.3 dated Oct. 2, 2018 4 pages.

Japanese Office Action Translation Application No. 2017-530139 dated Jul. 24, 2018 3 pages.

* cited by examiner

SYNTHESIS OF AMIDES AND AMINES FROM ALDEHYDES OR KETONES BY HETEROGENEOUS METAL CATALYSIS

CROSS-REFERENCE TO PRIOR APPLICATIONS

This application is a § 371 National Stage Application of PCT International Application No. PCT/EP2015/079869 filed Dec. 15, 2015, which claims priority to U.S. Provisional No. 62/091,912 filed Dec. 15, 2014, each of which are herein incorporated by reference in their entirety.

FIELD OF INVENTION

The present invention relates to eco-friendly methodology for the conversion of aldehydes or ketones to amines and amides by using a heterogeneous metal catalyst system. The invention further relate to a one-pot transformation of aldehydes or ketones into amides by using an amine donor for amination and a suitable acyl donor for amidation. The catalytic three-component transformation can also be employed for asymmetric synthesis.

BACKGROUND OF THE INVENTION

Amines and amides are useful and highly valuable compounds for the production of fine chemicals and pharmaceuticals. In this context, reductive amination is one of the most useful and versatile transformations for preparation of amines from carbonyl compounds in both nature and synthetic chemistry. In organic synthesis, it is attractive since aldehydes or ketones can be directly transformed in one-step to the corresponding primary or secondary alkyl amines without the need for isolation of the intermediate imines or hydroxylamines.[1]. In addition, the alkyl amine products are important due to their versatile utility as valuable synthons for pharmaceuticals and agrochemicals[2] as well as applications in chemical industries, materials science, and biotechnology.[3,4]

The Leuckart reaction is a classical process for the reductive amination of aldehydes or ketones by formamide, ammonium formate, or formic acid with formamide.[5] However, it suffers from several drawbacks (e.g. Requirement of high temperatures 150-240° C.), which lead to high consumption of energy and increase in production costs, formation of N-formyl derivatives, low chemoselectivity for synthesis of primary amines and long reaction times. Here the prolonged exposure to high temperatures of the reaction mixture inevitably leads to significant thermal decomposition of the components and consequently to lower yields of the products as well as difficulties with their isolation and purification. Moreover, production costs are increased. Therefore most of the current reductive amination procedures for the synthesis of primary amines are currently performed as two step combinations of the separate amination and reduction reactions. These two-step procedures can often take as much time as the traditional Leuckart reaction. Therefore, it is evident that there is a compelling need for fast and inexpensive methods for this classical reaction preferably under eco-friendly conditions.

Transition metal catalysts have been used for the synthesis of primary amines under the Leuckart-type reductive amination such as Rh, Ru and Ir.[6] It is noteworthy that the use of Pd/C as the catalyst leads to reduction of the carbonyl substrate to the corresponding methylene derivative.[7] However, palladium is arguably one of the most powerful and versatile transition-metal catalysts, which can be used for a variety of organic transformations and immobilized on various heterogeneous supports.[8] This could also lead to efficient recycling with consequent economic and environmental advantages. In this context, we recently developed synthetic methodology combining heterogeneous palladium catalysts with simple chiral amine co-catalysts.[9]

However, as can be seen above it would be highly challenging to develop new selective methodology for the efficient synthesis of primary amines from aldehydes or ketones using Leuckart-type conditions and a heterogeneous palladium catalyst (Scheme 1). There are serious chemoselectivity issues to take in to consideration. For example, the aldehydes 1 can be reduced either to the desired amines 2, dialkyl amine 2', alkanes 3 or alcohols 4. Furthermore, the aldehyde substrates can oligomerize or polymerize. This also the case for ketones.

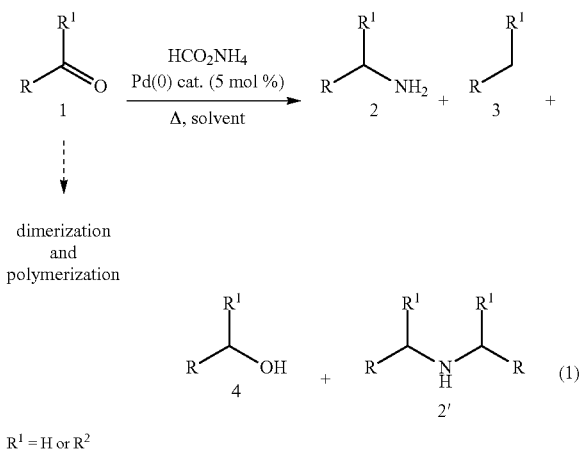

Scheme 1

One-pot multi-component reactions are of immense significance in biological and chemical systems.[10] It is also a part of green chemistry.[10b] The catalysis of these types of reactions using multi-catalyst systems involving heterogeneous catalysts has recently been disclosed.[11] Based on this, it could be possible to develop a novel one-pot three-component transformation for the direct formation of amides starting from aldehydes, ammonium formate and a suitable acyl donor. Here the integration of enzyme-catalyzed direct amidation of the in situ generated amines with unmodified acids would be attractive.[11b] In particular, applications towards the total synthesis of natural products are desirable aims.

For example, nonovamide 6a and capsaicin 6b are pungent naturally occurring amides that have been a part of the human diet of the Americas since minimum 7500 BC (chili pepper). They activate the TRPV1 receptor[12a,b] and a wide variety of physiological and biological activities induced by them have recently been reported.[12] Thus, the synthesis of capsaicin and its analogues could be achieved by an initial efficient primary amine 2 synthesis from the aldehyde 1 using a heterogeneous metal catalyst followed by reaction with acyl chlorides to form the final products 6. Alternatively amidation can be accomplished by an enzyme-catalyzed reaction between amine 2 and different acid derivatives.

Another application of the technology is its employment for asymmetric synthesis. Here the ketone is converted to the corresponding chiral amides using the same strategies and a suitable condition. The enzyme/heterogeneous metal-catalyzed step, depending on the choice of reaction conditions, could either convert the ketone by asymmetric synthesis to the corresponding optical active amide or both this amide and an optical active amine with the opposite absolute stereochemistry.

OBJECT OF THE INVENTION

A first object of the invention is to synthesize amides from aldehydes and ketones.

A second object of the invention is the total synthesis of capsaicinoids starting from vanillin or vanilyl alcohol and their derivatives.

A third object of the invention is the direct in situ conversion of aldehydes or ketones to amides, which have been generated by catalytic oxidation of the starting alcohol.

A fourth object of the invention to synthesize amines from aldehydes and ketones.

A still further objective of the invention is to provide a method of the aforementioned kind that is advantageous from an environmental and health standpoint.

SUMMARY OF THE INVENTION

The invention is based on the use of a heterogeneous metal catalyst system that can convert aldehydes or ketones to amines using a suitable amine donor and reducing agent (according to Scheme 2).

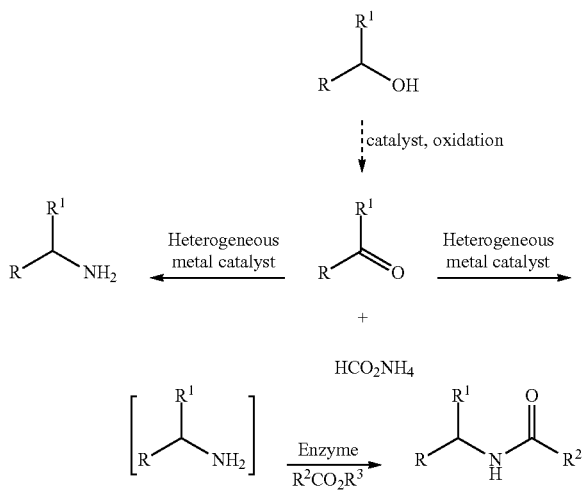

Scheme 2

Another aspect of the invention is the use of a heterogeneous metal catalyst system that when integrated with an acyl donor can convert aldehydes or ketones in the presence of an amine donor and reducing agent to amides in sequence or in one-pot, respectively (according to Scheme 3).

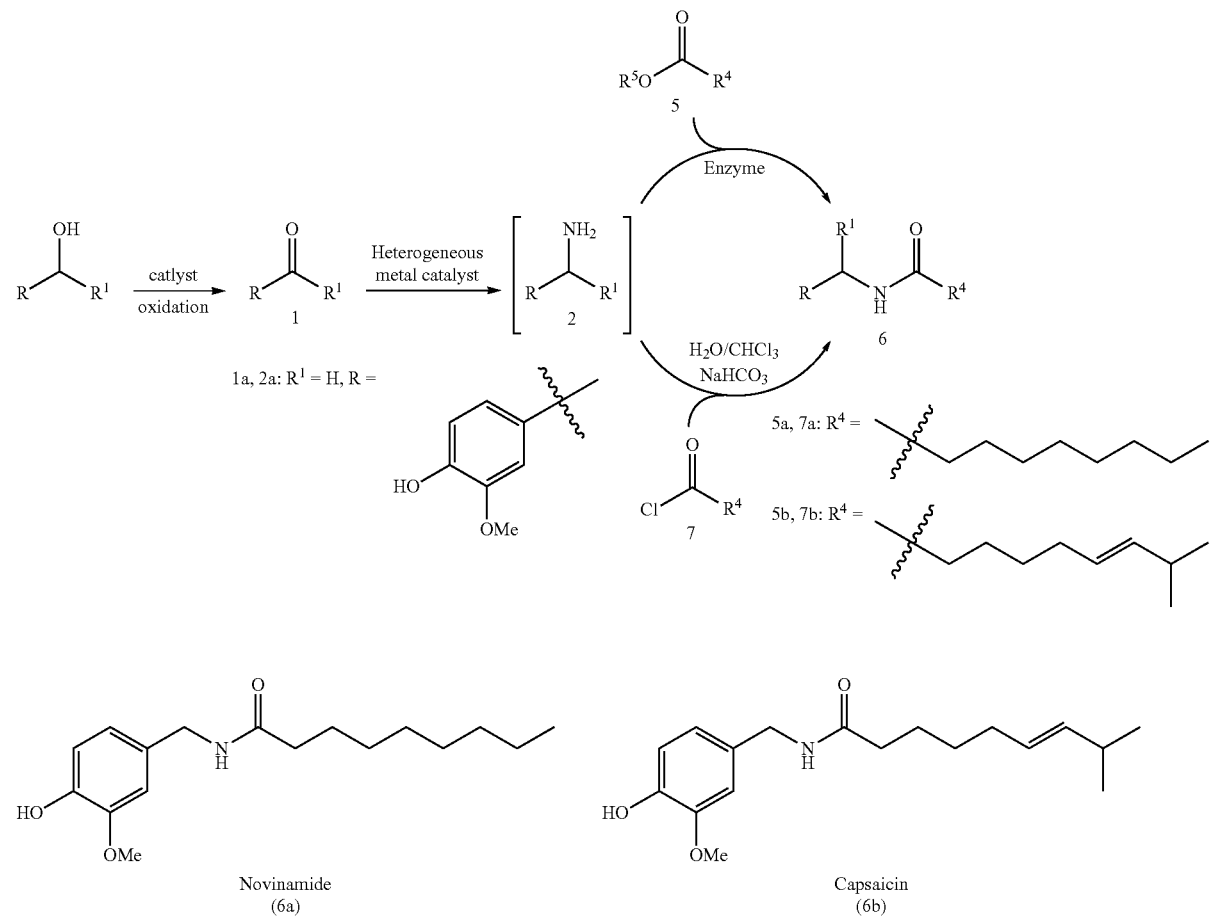

Scheme 3

Another aspect of the invention is the use of a heterogeneous metal catalyst system that when integrated with another catalytic system (e.g. enzyme catalyst) can convert aldehydes and ketones to amides in sequence or in one-pot, respectively (according to Scheme 2).

Another aspect of the invention is the use of a heterogeneous catalyst system that when integrated with other catalytic systems (e.g. heterogeneous metal, homogeneous and an organic catalyst) can convert alcohols to amines and amides via the generated aldehydes or ketones respectively in sequence or in one-pot, respectively (according to Scheme 2).

Another, aspect of the invention is the synthesis of capsaicinoids and similar derivatives starting from vanillin or vanillyl alcohol and their derivatives using a heterogeneous metal catalyst, suitable amine donor, reducing agent and acyl donor (according to Scheme 3).

Another, aspect of the invention is the use of a heterogeneous metal catalyst system that when integrated with another catalytic system (e.g. enzyme catalyst) can convert ketones to optically active chiral amides (according to Scheme 4).

Scheme 4

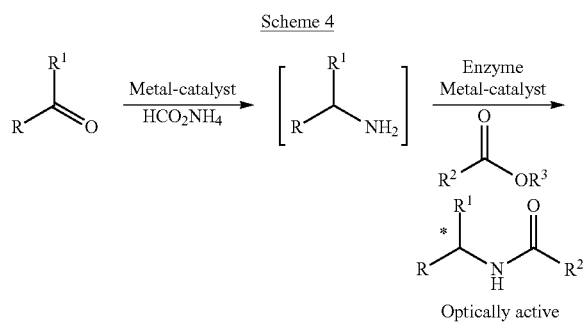

Another, aspect of the invention is the use of a heterogeneous metal catalyst system that when integrated with another catalytic system (e.g. enzyme catalyst) can convert ketones to optically active chiral amines and Scheme 5

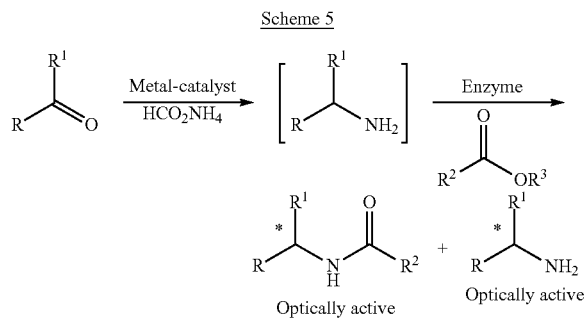

amides (according to Scheme 5).

The first object of the invention is achieved by a method for conversion of an aldehyde or ketone comprising the steps of:
Providing an aldehyde or a ketone,
Converting the aldehyde or ketone to an amine,
Converting the amine to an amide,
wherein the conversion to amine and/or amide is catalyzed by a heterogeneous metal catalyst.

In a further preferred embodiment of the invention, said conversion is a one-pot synthesis. Preferably, said conversion is performed in one pot without any purification of intermediates.

In a preferred embodiment of the invention, the aldehyde is of formula

wherein R is selected from substituted or unsubstituted alkyl, cycloalkyl, aryl, cinnamyl and heterocyclic groups.

In a further preferred embodiment of the invention, the ketone is of formula

wherein R and $R^1$ are selected from substituted or unsubstituted alkyl, cycloalkyl, aryl and heterocyclic groups.

In a further preferred embodiment of the invention, the heterogeneous metal catalyst is a heterogeneous palladium (Pd) catalyst, preferably a Pd(0) catalyst, more preferably a Pd(0)-nanoparticle catalyst.

In a further preferred embodiment of the invention, the heterogeneous palladium catalyst is selected from $Pd^0$-AmP-MCF (palladium(0)-aminopropyl-mesocellular foam) and $Pd^0$-AmP-CPG (palladium(0)-aminopropyl-controlled pore glass).

In a further preferred embodiment of the invention, the step of converting the aldehyde or ketone to an amine is catalyzed by a heterogeneous metal catalyst in the presence of an amine donor and reducing agent.

In a further preferred embodiment of the invention, the amine donor is selected from:
ammonium formate ($HCO_2NH_4$) or a derivative thereof, and
amine.

In a further preferred embodiment of the invention, the reducing agent is selected from:
ammonium formate ($HCO_2NH_4$) or a derivative thereof, formic acid, and
$H_2$.

In a further preferred embodiment of the invention, ammonium formate ($HCO_2NH_4$) is the amine donor and reducing agent.

In a further preferred embodiment of the invention, the step of converting the aldehyde or ketone to an amine is carried out at a temperature of at least 22° C., preferably at 60-100° C., wherein the an organic solution is used as a solvent.

In a further preferred embodiment of the invention, the step of converting the amine to an amide is carried out in the presence of an acyl donor, wherein said acyl donor is an acylating agent selected from acids, esters, alkyl ketene dimers, acid chlorides and anhydrides.

In a further preferred embodiment of the invention, the step of converting the amine to an amide is catalyzed by a heterogeneous metal catalyst and/or an enzyme.

In a further preferred embodiment of the invention, the step of converting the amine to an amide is catalyzed by a heterogeneous metal catalyst and an enzyme.

In a further preferred embodiment of the invention, the step of converting the aldehyde or ketone to an amine is catalyzed by Pd$^0$-AmP-MCF or Pd$^0$-AmP-CPG, whereas the step of converting the amine to an amide is catalyzed by Pd$^0$-AmP-MCF and enzyme in the presence of acyl donor.

In a further preferred embodiment of the invention, the enzyme is selected from lipase and amine transaminase (ATA), wherein the lipase is preferably lipase B, more preferably the lipase is CALB (*Candida antarctica* lipase B), and wherein the amine transaminase is preferably selected from ATA-117, ATA-113 and CV-ATA (*Chromobacterium violacum* ATA).

In a further preferred embodiment of the invention, the enzyme is lipase, preferably lipase B, more preferably lipase B is CALB (*Candida antarctica* lipase B).

In a further preferred embodiment of the invention, lipase B is immobilized on a macroporous anionic resin.

In a further preferred embodiment of the invention, the enzyme is ATA, preferably selected from ATA-117, ATA-113 and CV-ATA (*Chromobacterium violacum* ATA), more preferably (R)-selective ATA or (S)-selective ATA.

In a further preferred embodiment of the invention,
the step of converting the aldehyde or ketone to an amine is catalyzed by Pd$^0$-AmP-MCF or Pd$^0$-AmP-CPG, and wherein methanol or toluene is used as solvent,
the step of converting the amine to an amide is catalyzed by Pd$^0$-AmP-MCF and enzyme in the presence of acyl donor, wherein the enzyme is preferably selected from lipase and ATA, and wherein
toluene is used as solvent.

In a further preferred embodiment of the invention,
the step of converting the aldehyde or ketone to an amine is catalyzed by Pd$^0$-AmP-MCF or Pd$^0$-AmP-CPG, and wherein toluene is used as solvent,
the step of converting the amine to an amide is catalyzed by Pd$^0$-AmP-MCF and lipase B in the presence of acyl donor, and wherein
toluene is used as solvent.

In a further preferred embodiment of the invention,
the step of converting the aldehyde or ketone to an amine comprises the steps of mixing a ketone or aldehyde with ammonium formate and Pd$^0$-AmP-MCF or Pd$^0$-AmP-CPG in toluene, and subsequently stirring at a temperature of at least 22° C. for at least 1 hour, preferably at 60-100 C.°, and wherein the reaction is carried for at least 1 hour, preferably for 1.5-7 hours, more preferably for 2.5-3.5 hours,
the step of converting the amine to an amide comprises the steps of:
  adding lipase B and optionally an additive, wherein the additive is preferably molecular sieve, wherein the molecular sieve preferably has a diameter of 4 Å,
  adding an acyl donor, wherein the acyl donor is preferably an acid, and
  mixing at a temperature of at least 22° C., preferably at 60-100 C.°, for at least 1 hour, preferably for 36 hours.

In a further preferred embodiment of the invention,
the step of converting the aldehyde or ketone to an amine is catalyzed by Pd$^0$-AmP-MCF and wherein methanol is used as solvent,
the step of converting the amine to an amide is catalyzed by Pd$^0$-AmP-MCF and enzyme in the presence of acyl donor, wherein the enzyme is preferably lipase B, more preferably the enzyme is CALB, and wherein
toluene is used as solvent in the amidation step.

In a further preferred embodiment of the invention,
the step of converting the aldehyde or ketone to an amine is catalyzed by Pd$^0$-AmP-MCF, ammonium formate is the amine donor, methanol is the solvent, wherein the reaction is carried out at least 22° C., preferably at 60-100 C.°, and wherein the reaction is carried for at least 1 hour, preferably for 1.5-7 hours, more preferably for 1.5-4.5 hours.
the step of converting the amine to an amide is catalyzed by Pd$^0$-AmP-MCF and enzyme in the presence of acyl donor, wherein the enzyme is preferably lipase B, more preferably the enzyme is CALB, and wherein
toluene is used as solvent in the amidation step.

In a further preferred embodiment of the invention,
the step of converting the aldehyde or ketone to an amine is catalyzed by Pd$^0$-AmP-MCF, ammonium formate is the amine donor, methanol is the solvent, wherein the reaction is carried out at least 22° C., preferably at 60-100° C., and wherein the reaction is carried for at least 1 hour, preferably for 1.5-7 hours, more preferably for 1.5-4.5 hours.
the step of converting the amine to an amide is catalyzed by Pd$^0$-AmP-MCF and lipase B, wherein lipase b is preferably CALB, and wherein
toluene is used as solvent in the amidation step.

In a further preferred embodiment of the invention,
the step of converting the aldehyde or ketone to an amine comprises the steps of mixing a ketone or aldehyde with ammonium formate and Pd$^0$-AmP-MCF in methanol, and subsequently stirring at a temperature of at least 22° C. for at least 1 hour, preferably at 60-100 C.°, and wherein the reaction is carried for at least 1 hour, preferably for 1.5-7 hours, more preferably for 1.5-4.5 hours, wherein the step of converting the aldehyde or ketone to an amine is preferably carried out under N$_2$ atmosphere,
the step of converting the amine to an amide comprises the steps of:
  evaporating the solvent,
  adding Pd$^0$-AmP-MCF,
  adding CALB and optionally an additive, wherein the additive is preferably molecular sieve or Na$_2$CO$_3$, wherein the molecular sieve preferably has a diameter of 4 Å, and wherein Na$_2$CO is preferably dry Na$_2$CO$_3$
  adding toluene under H$_2$ atmosphere,
  adding an acyl donor under H$_2$ atmosphere, and
  mixing under H$_2$ atmosphere, preferably for at least 1 hour, more preferably for 6, 12 or 16 hours.

In a further preferred embodiment of the invention,
the step of converting the aldehyde or ketone to an amine comprises the steps of mixing a ketone or aldehyde with ammonium formate and Pd$^0$-AmP-MCF in methanol, and subsequently stirring at a temperature of at least 22° C. for at least 1 hour, preferably at 60-100 C.°, and wherein the reaction is carried for at least 1 hour, preferably for 1.5-7 hours, more preferably for 1.5-4.5 hours, wherein the step of converting the aldehyde or ketone to an amine is preferably carried out under N$_2$ atmosphere,
the step of converting the amine to an amide comprises the steps of:
  evaporating the solvent,
  adding Pd$^0$-AmP-MCF,
  adding CALB and additive, wherein the additive is preferably molecular sieve or Na$_2$CO$_3$, wherein the molecular sieve preferably has a diameter of 4 Å, and wherein Na$_2$CO is preferably dry Na$_2$CO, adding toluene under H$_2$ atmosphere,
adding an acyl donor under H$_2$ atmosphere, and
mixing under H$_2$ atmosphere, preferably for at least 1 hour, more preferably for 6, 12 or 16 hours.

In a further preferred embodiment of the invention,
the step of converting the aldehyde or ketone to an amine comprises the steps of mixing a ketone or aldehyde with ammonium formate and 1 mol % Pd$^0$-AmP-MCF in methanol, and subsequently stirring at a temperature of at least 22° C. for at least 1 hour, preferably at 60-100 C.°, and wherein the reaction is carried for at least 1 hour, preferably for 1.5-7 hours, more preferably for 1.5-4.5 hours, wherein the step of converting the aldehyde or ketone to an amine is preferably carried out under N$_2$ atmosphere, the step of converting the amine to an amide comprises the steps of:
evaporating the solvent,
adding 4 mol % Pd$^0$-AmP-MCF,
adding CALB and molecular sieve, wherein the molecular sieve preferably has a diameter of 4 Å,
adding toluene under H$_2$ atmosphere,
adding an acyl donor under H$_2$ atmosphere, and
mixing under H$_2$ atmosphere, preferably for at least 1 hour, more preferably for 6, 12 or 16 hours.

In a further preferred embodiment of the invention, the acyl donor is ethyl methoxyacetate.

The method according to the invention, in a further preferred embodiment of the invention, of structural formula

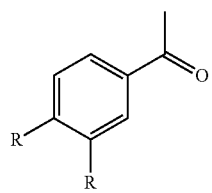

wherein R is selected from H, alkoxy or alkyl, and wherein the resulting amide is of structural formula

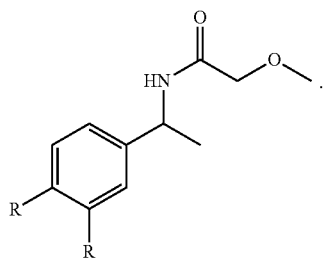

or wherein the substituents R are identical and wherein R is either H or methoxy.

In a further preferred embodiment of the invention, each R is selected from H, methoxy or methyl and the resulting amide is selected from the following amides:

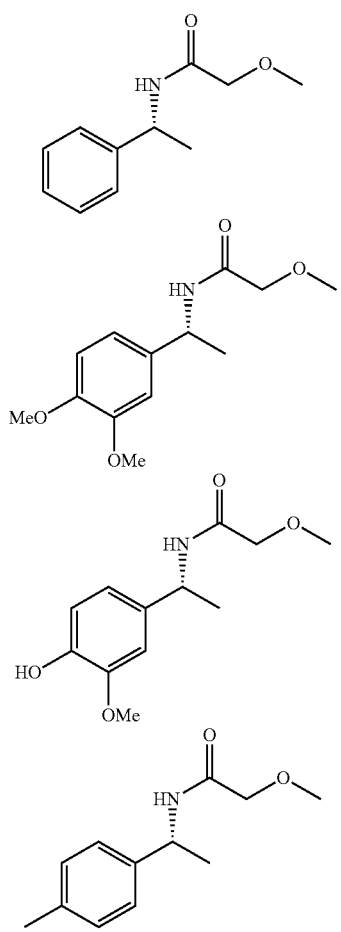

In a further preferred embodiment of the invention,
the step of converting the ketone to an amine comprises the steps of mixing a ketone with ammonium formate and Pd$^0$-AmP-MCF in methanol, and subsequently stirring at a temperature of at least 22° C. for at least 1 hour, preferably at 60-100 C.°, and wherein the reaction is carried for at least 1 hour, preferably for 1.5-7 hours, more preferably for 1.5-4.5 hours, wherein the step of converting the ketone to an amine is preferably carried out under N$_2$ atmosphere, the step of converting the amine to an amide comprises the steps of:
evaporating the solvent,
adding DIPEA,
adding an organic solvent, preferably the organic solvent is dichloromethane,
adding an acyl donor, preferably the acyl donor is methoxy acetylchloride, and
mixing, preferably for at least 1 hour, more preferably overnight.

In a further preferred embodiment of the invention, the ketone is of structural formula

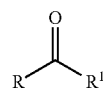

selected from:
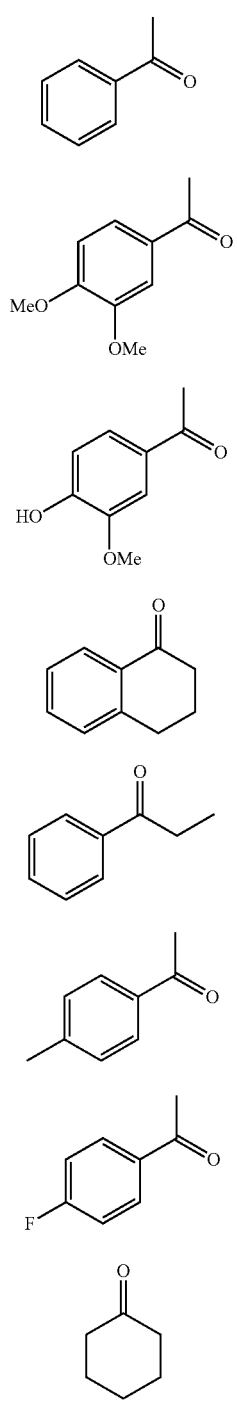
wherein the corresponding resulting amine in the amination step is of structural formula
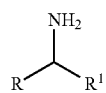
selected from:
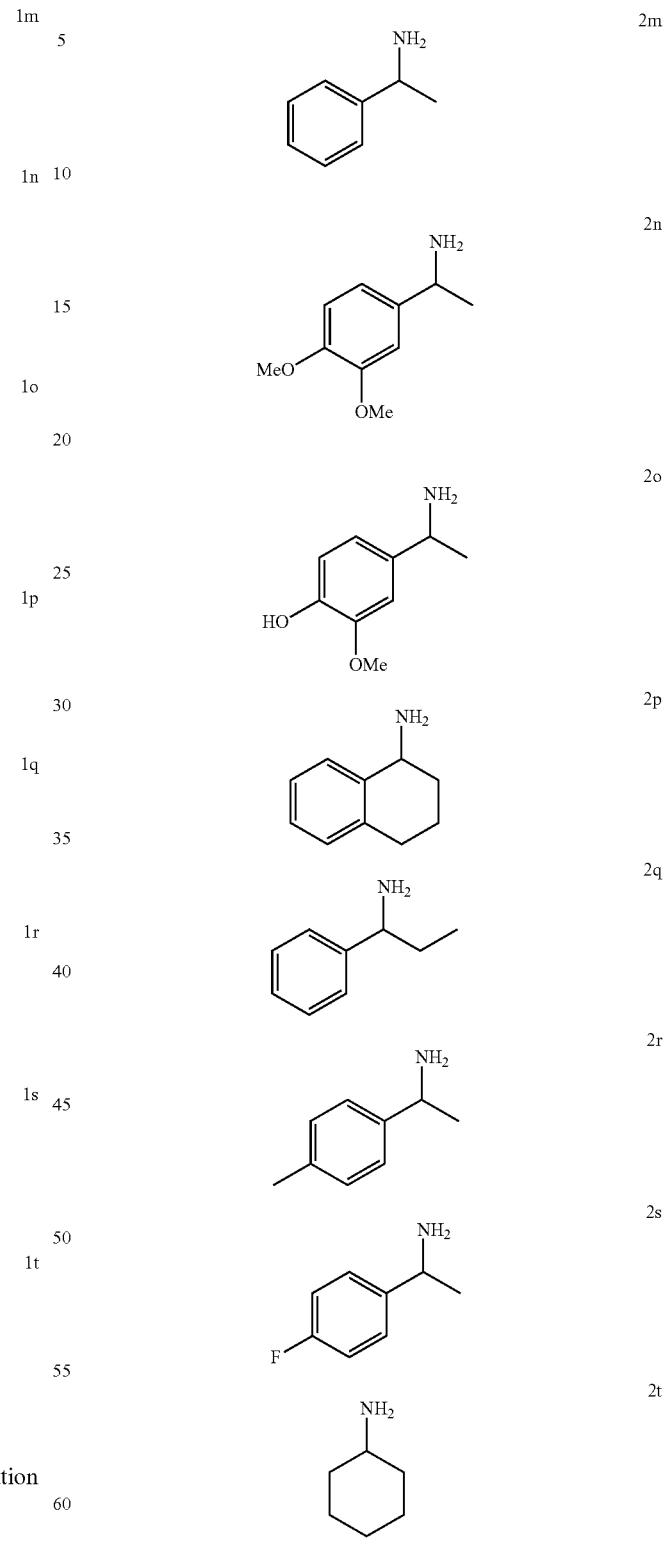
wherein the amino group of the above amine is in the amidation step acylated with a methoxyacetyl group and thereby the resulting amide in the amidation step is of formula

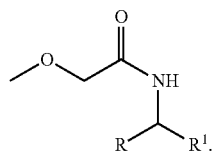

In a further preferred embodiment of the invention, the step of converting the aldehyde or ketone to an amine comprises the steps of mixing a ketone or aldehyde with ammonium formate and Pd$^0$-AmP-MCF in methanol, and subsequently stirring at a temperature of at least 22° C. for at least 1 hour, preferably at 60-100 C.°, and wherein the reaction is carried for at least 1 hour, preferably for 1.5-7 hours, more preferably for 1.5-4.5 hours, preferably under $N_2$ atmosphere, the step of converting the amine to an amide comprises the steps of:

optionally putting the mixture on ice, adding methanol to the mixture, adding ATA and acyl donor, mixing for at least 1 hour, more preferably for 24 hours, wherein the mixing is preferably conducted in darkness.

In a further preferred embodiment of the invention, the step of converting the aldehyde or ketone to an amine comprises the steps of mixing a ketone or aldehyde with ammonium formate and Pd$^0$-AmP-MCF in methanol, and subsequently stirring at a temperature of at least 22° C. for at least 1 hour, preferably at 60-100 C.°, and wherein the reaction is carried for at least 1 hour, preferably for 1.5-7 hours, more preferably for 1.5-4.5 hours, preferably under $N_2$ atmosphere, the step of converting the amine to an amide comprises the steps of:

putting the mixture on ice, adding methanol to the mixture, adding (R)-selective ATA or (S)-selective ATA, adding acyl donor, wherein the acyl donor is preferably sodium pyruvate.

mixing for at least 1 hour, more preferably for 24 hours, wherein the mixing is preferably conducted in darkness.

The second object of the invention is achieved when the above disclosed preferred conversions are conducted with an aldehyde of structural formula

wherein R is selected from one of the following substituents:

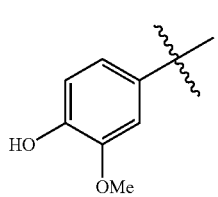 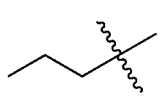

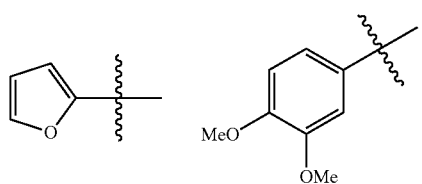

In a preferred embodiment, the acyl donor is an acid of structural formula

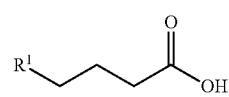

In a further preferred embodiment, $R^1$ is selected from one of the following substituents:

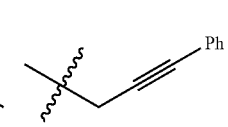

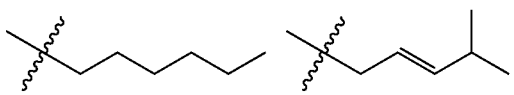

In a further preferred embodiment, the resulting product is an amide of structural formula

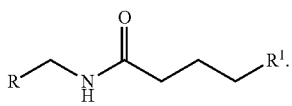

In a further preferred embodiment, the resulting product is novinamide, capsaicin or phenylcapsaicin having the following respective structural formula:

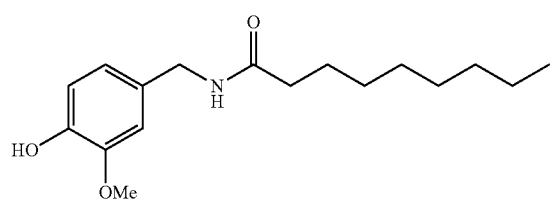

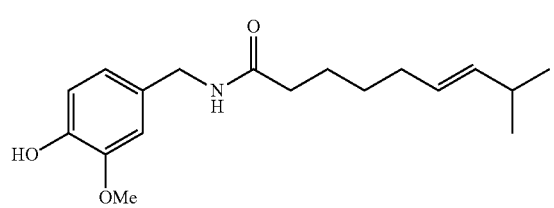

-continued

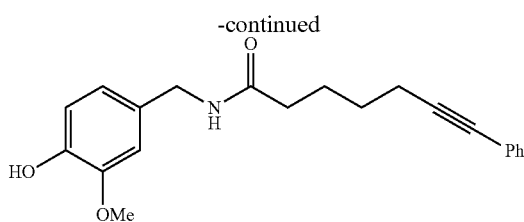

The third object of the invention is achieved when an aldehyde or a ketone is provided by reacting an alcohol with Pd⁰-AmP-CPG in the presence of $O_2$, wherein said alcohol is selected from a primary alcohol, secondary alcohol and aldol. Preferably said alcohol is vanillyl alcohol, more preferably said alcohol is vanillyl alcohol derived from lignin.

The fourth object of the invention is achieved by the steps of converting the aldehyde or ketone to an amine disclosed in the above preferred embodiments of the first object of the invention.

DETAILED DESCRIPTION

The present invention relates to a method for conversion of an aldehyde or ketone to an amine or an amide. The method comprises the steps of (i) providing an aldehyde or a ketone, (ii) converting the aldehyde or ketone to an amine, and (iii) converting the amine to an amide. The conversion to an amine compound, as well as the conversion to an amide compound, is catalyzed by a heterogeneous metal catalyst. One of the advantages of the method is that it is a one-pot synthesis.

The aldehyde which is used in the conversion method may be of formula

wherein R is selected from substituted or unsubstituted alkyl, cycloalkyl, aryl, cinnamyl and heterocyclic groups.

The ketone which may be used is of formula

wherein R and R1 are selected from substituted or unsubstituted alkyl, cycloalkyl, aryl and heterocyclic groups.

The heterogeneous metal catalyst may be a heterogeneous palladium (Pd) catalyst such as a Pd(0) catalyst or Pd(0)-nanoparticle catalyst. Preferred heterogeneous palladium catalysts are Pd⁰-AmP-MCF (palladium(0)-aminopropyl-mesocellular foam) and Pd⁰-AmP-CPG (palladium(0)-aminopropyl-controlled pore glass).

The conversion of an aldehyde or ketone to an amine is catalyzed by a heterogeneous metal catalyst in the presence of an amine donor and reducing agent. The amine donor can be (i) ammonium formate ($HCO_2NH_4$) or a derivative thereof, or (i) an amine. The reducing agent can be selected (i) ammonium formate ($HCO_2NH_4$) or a derivative thereof, (ii) formic acid, or (iii) $H_2$. In a preferred embodiment, ammonium formate is the amine donor as well as the reducing agent.

The reaction step of converting the aldehyde or ketone to an amine is carried out at a temperature of at least 22° C. The best yields are achieved when the temperature is at 60-100° C. An organic solvent such as methanol or toluene may be used in the amination step.

The reaction step of converting the amine to an amide is carried out in the presence of an acyl donor. The acyl donor may be an acylating agent selected from acids, esters, alkyl ketene dimers, acid chlorides and anhydrides. The amidation step maybe catalyzed by a heterogeneous metal catalyst and/or an enzyme.

Preferably, the step of converting the aldehyde or ketone to an amine is catalyzed by Pd⁰-AmP-MCF or Pd⁰-AmP-CPG, whereas the step of converting the amine to an amide is catalyzed by Pd⁰-AmP-MCF and enzyme in the presence of acyl donor. The enzyme may be lipase or an amine transaminase (ATA). Lipase B such as CALB (*Candida antarctica* lipase B) is particularly preferred. Moreover, lipase B immobilized on a macroporous anionic resin may also be used. The amine transaminase is preferably selected from ATA-117, ATA-113 and CV-ATA (*Chromobacterium violacum* ATA). Additionally, (R)-selective ATA or (S)-selective ATA can be used for preparing optically active chiral amines.

The following examples provide various methods for preparing amines and amides from aldehydes and ketones, as well as from alcohols.

GENERAL EXPERIMENTAL CONDITION

Chemicals and solvents were either purchased puriss p. A. from commercial suppliers or were purified by standard techniques. Commercial reagents were used as purchased without any further purification.

Aluminum sheet silica gel plates (Fluka 60 F254) were used for thin-layer chromatography (TLC), and the compounds were visualized by irradiation with UV light (254 nm) or by treatment with a solution of phosphomolybdic acid (25 g), $Ce(SO_4)_2$—$H_2O$ (10 g), conc. $H_2SO_4$ (60 mL), and $H_2O$ (940 mL), followed by heating. Purification of the product was carried out by flash column chromatography using silica gel (Fluka 60, particle size 0.040-0.063 mm).

The Pd⁰-AmP-MFC (8.25 wt % Pd) and Pd⁰-AMP-CPG (2.05 wt % Pd) catalysts were prepared according to previously reported procedures.

Infrared (IR) spectra were recorded on Thermo Fisher Nicolet 6700 FT-IR spectrometer, $\bar{u}_{max}$ in $cm^{-1}$. Bands are characterized as broad (br), strong (s), medium (m), or weak (w). ¹H NMR spectra were recorded on a Bruker Avance (500 MHz) spectrometer. Chemical shifts are reported in ppm from tetramethylsilane with the solvent resonance resulting from incomplete deuterium incorporation as the internal standard ($CDCl_3$: δ 7.26 ppm). Data are reported as follows: chemical shift, multiplicity (s=singlet, d=doublet, q=quartet, br=broad, m=multiplet), and coupling constants (Hz), integration. ¹³C NMR spectra were recorded on a Bruker Avance (125.8 MHz or 100 MHz) spectrometer with complete proton decoupling, Chemical shifts are reported in ppm from tetramethylsilane with the solvent resonance as the internal standard ($CDCl_3$: δ 77.16 ppm). High-resolution mass spectrometry was performed on Agilent 6520 Accurate-Mass Q-TOF LC/MS (positive mode).

Example 1—Screening for Heterogeneous Metal Catalyst

Initial screening studies was conducted by using vanillin 1a as the model substrate. Vanillin can be produced from the renewable resource lignin. Ammonium formate ($HCO_2NH_4$) was used as the amine donor and reducing agent in the presence of different palladium catalysts as indicated in Table 1.

TABLE 1

Optimization of reductive amination reaction.

| Entry | Catalyst | HCO$_2$NH$_4$ (equiv.) | temp. (° C.) | time (h) | Conv. (%)[a] | Ratio (2a:6a:5a)[a] |
|---|---|---|---|---|---|---|
| 1 | Pd(0)-AmP-MCF | 3 | 22 | 12 | 90 | 38:62:0 |
| 2 | — | 3 | 80 | 24 | <1 | — |
| 3 | Pd(0)-AmP-MCF | 2 | 80 | 2.5 | >99 | 88:12:0 |
| 4 | Pd(0)-AmP-MCF | 3 | 80 | 2.5 | >99 | 94:6:0 |
| 5 | Pd(0)-AmP-MCF | 3 | 60 | 7 | >99 | 86:14:0 |
| 6 | Pd(PPh$_3$)$_4$ | 3 | 80 | 24 | <1 | — |
| 7 | Pd(0)-AmP-CPG[c] | 3 | 80 | 2.5 | >95 | 81:15:4 |
| 8 | Pd(0)-AmP-CPG | 3 | 80 | 2.5 | >95 | 79:14:7 |
| 9 | Pd(OH)$_2$/C | 3 | 80 | 20 | >99 | 55:45:0 |
| 10 | Pd/C | 3 | 80 | 20 | >99 | 34:60:6 |
| 11 | Pd(OAc)$_2$ | 3 | 80 | 20 | >99 | 39:38:23 |
| 12[b] | Pd(0)-AmP-MCF | 3 | 80 | 12 | >99 | 42:5:53 |

[a]Determined by $^1$H-NMR analysis of the crude reaction mixture.
[b]The reaction was run with molecular sieve 4Å.
[c]6.6 mol % cat.

For example, aldehyde 1a was converted to the desired amine 2a in poor chemoselectivity together with significant amounts of 6a in the presence of palladium(0)-aminopropyl-mesocellular foam (Pd$^0$-AmP-MCF, 5 mol %) in toluene at room temperature (entry 1). Increasing the temperature significantly accelerated the reaction as well as switched the chemoselectivity towards amine 2a formation (entries 3-5). This was also the case when employing palladium(0)-aminopropyl-controlled pore glass (Pd$^0$-AmP-CPG) as the catalyst (entry 7). The use of other commercially available heterogeneous and homogeneous Pd catalysts resulted in low chemoselectivity (entries 9-11). Moreover, the same relay sequence using homogeneous Pd(PPh$_3$)$_4$ as catalyst or performing the reaction in the absence of a palladium source did not deliver amine 2a (only starting material was detected, entries 2 and 6).

General Procedure for the Screening:

To a microwave-vial containing the Pd$^0$-catalyst (5 mol %) and ammonium formate (37.8 mg, 0.6 mmol, 3.0 equiv.) was added the solid vanillin 1a (0.2 mmol, 1.0 equiv.) under N$_2$ atmosphere. Next, toluene (1 mL) was added at room temperature. The temperature was then set to the one shown in Table 1 and the reaction mixture was stirred under N$_2$ atmosphere. After the time shown in Table 1, the crude reaction mixture was filtrated through Celite using CHCl$_3$ (10 mL) as eluent and evaporated. The crude material was purified by silica gel flash column chromatography. NMR samples for NMR-yield were prepared by removing 0.05 mL aliquots from the reaction mixtures, filtration through Celite using CDCl$_3$ (1.5 mL) as eluent and mesitylene as the internal standard.

Example 2—Synthesis of Amines

With these results in Example 1 at hand, the scope of the catalytic amination of a range of aldehydes using Pd$^0$-Amp-MCF or Pd$^0$-Amp-CPG (6.6 mol %) as the heterogeneous catalysts was investigated. Ammonium formate (3 equiv) was used as amine donor and reducing agent. The reaction was carried out at 80° C. in toluene and the results are shown in Table 2.

TABLE 2

Examples of prepared amines

R–CHO  →  R–CH$_2$–NH$_2$
1          2

Pd(0) cat. (5 mol %), HCO$_2$NH$_4$ (3 equiv.), toluene, 80° C.

| Entry | Pd(0) cat. | R | Time (h) | Product | Yield (%)[a] |
|---|---|---|---|---|---|
| 1 | Pd(0)-AmP-MCF | 4-hydroxy-3-methoxyphenyl | 2.5 | 2a | 87 |
| 2 | Pd(0)-AmP-CPG[c] | 4-hydroxy-3-methoxyphenyl | 2.5 | 2a | 78 |
| 3 | Pd(0)-AmP-MCF | phenyl | 3 | 2b | 85 |
| 4 | Pd(0)-AmP-MCF | phenethyl | 3 | 2c | 92[b] |
| 5 | Pd(0)-AmP-MCF | n-Pent | 4 | 2d | 91[b] |
| 6 | Pd(0)-AmP-CPG[c] | n-Pent | 3.5 | 2d | 87[b] |
| 7 | Pd(0)-AmP-MCF | n-Octyl | 4 | 2e | 78 |
| 8 | Pd(0)-AmP-MCF | 4-methoxyphenyl | 4 | 2f | 85 |
| 9 | Pd(0)-AmP-CPG[c] | 4-methoxyphenyl | 4 | 2f | 76 |
| 10 | Pd(0)-AmP-MCF | cyclohexyl | 3 | 2g | 90 |
| 11 | Pd(0)-AmP-MCF | 2-furyl | 3 | 2h | 71[b] |
| 12 | Pd(0)-AmP-MCF | benzo[1,3]dioxol-5-yl | 3 | 2i | 72 |

TABLE 2-continued

Examples of prepared amines

R–CHO  →[Pd(0) cat. (5 mol %)][HCO$_2$NH$_4$ (3 equiv.), toluene, 80° C.] R–CH$_2$NH$_2$
  1                                                                          2

| Entry | Pd(0) cat. | R | Time (h) | Product | Yield (%)[a] |
|---|---|---|---|---|---|
| 13 | Pd(0)-AmP-MCF | Et | 3 | 2j | 93[b] |
| 14 | Pd(0)-AmP-MCF | CO$_2$Et | 3 | 2k | 55[d] |
| 15 | Pd(0)-AmP-MCF | 4-F-C$_6$H$_4$-CH(Me)- | 3.5 | 2l | 63 |

[a] Isolated yield of pure 2.
[b] 1H-NMR yield using mesitylene as internal standard.
[c] 6.6 mol % cat.
[d] 1 (0.4 mmol).

The reactions were highly chemoselective and a variety of aldehydes were converted to the corresponding amines and glycine derivative 2a-2l. (55-93% yield, Table 2). Notably, the transformation was chemospecific towards amine 2-formation when aliphatic aldehydes were used as substrates. The total synthesis of natural products is a highly desirable aim. Here, nonivamide 3a and capsaicin 3b are pungent amides that have been a part of the human diet of the Americas since minimum 7500 BC (chili pepper). They activate the TRPV1 receptor and a wide variety of physiological and biological activities induced by them have recently been reported. According to Scheme 6 they should be possible to assemble via a heterogeneous metal/enzyme reductive amination/amidation or aerobic oxidation/reductive amination/amidation sequence.

Scheme 6

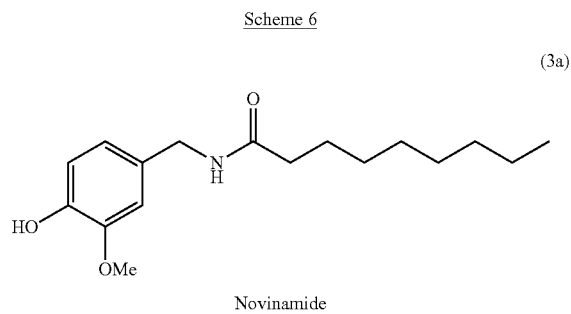
Novinamide (3a)

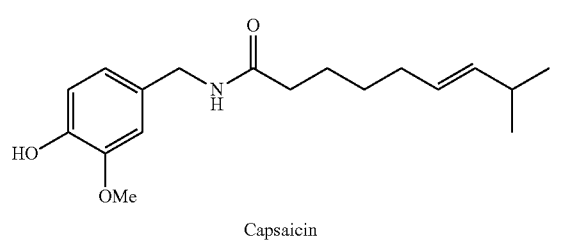
Capsaicin (3b)

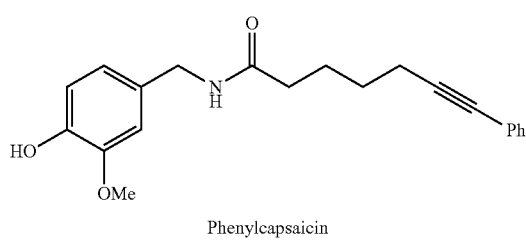
Phenylcapsaicin (3c)

General Procedure for the Synthesis of Amines:

To a microwave-vial containing the Pd$^0$-catalyst (Pd$^0$-AmP-MFC, 13.4 mg, 0.01 mmol, 8.25 wt %, 5 mol %) or (Pd$^0$-CPG, 569 Å, 74.0 mg, 0.013 mmol, 2.05 wt %, 6.6 mol %) and ammonium formate (37.8 mg, 0.6 mmol, 3.0 equiv.) was added the solid 1 (0.2 mmol, 1.0 equiv.) under N$_2$ atmosphere. Next, toluene (1 mL) was added at room temperature. If the aldehyde substrate was a liquid it was added after the addition of toluene. The temperature was then increased and the reaction mixture was stirred 80° C. for the time shown in Table 2 under N$_2$ atmosphere. Before the purification of the products, the crude reaction mixture was filtrated through Celite using CHCl$_3$ (10 mL) as eluent and evaporated. The crude material was purified by silica gel flash column chromatography to give the corresponding amines 2. NMR samples for NMR-yield were prepared by removing 0.05 mL aliquots from the reaction mixtures, filtration through Celite using CDCl$_3$ (1.5 mL) as eluent and mesitylene as the internal standard. The hexan-1-amine 2d, furan-2-ylmethanamine 2h and propan-1-amine 2j were directly acylated by Novozyme 435 to the corresponding amides and then isolated by silica gel column chromatography (See Table 2).

Example 3—Reductive Amination/Amidation Catalytic Relay

With these results in Example 1 at hand, a one-pot co-catalytic reaction between aldehyde 1a, HCO$_2$NH$_4$ and nonanoic acid 4a using commercially available *Candida antarctica* lipase B (Novozyme-435, CALB) immobilized on a macroporous resin as the co-catalyst was developed. CALB was chosen as the catalyst for its ability to amidate 2a. The one-pot co-catalytic relay sequence gave nonivamide 3a in high yield (74%) using a Pd(0)-nanoparticle and enzyme catalyst system. However, no amide 3a was formed if either the enzyme or the Pd catalyst was absent. Thus, the enzyme and the Pd-catalyst operated synergistically during the in situ amidation step. The scope of the co-catalytic one-pot cascade transformation sequence and the total synthesis of capsaicin 3b and "phenylcapsaicin" 3c were next investigated as indicated in Table 3.

TABLE 3

Reductive amination/amidation catalytic relay.

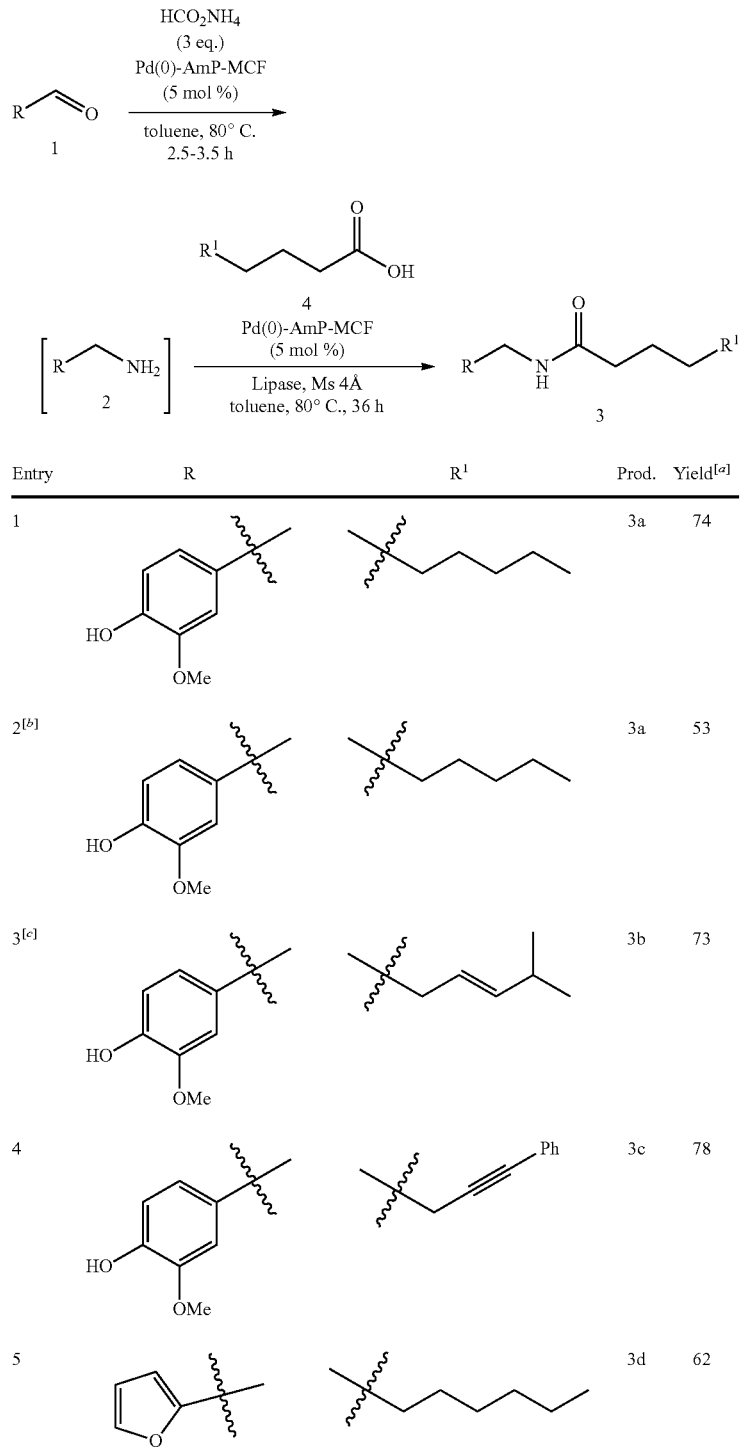

TABLE 3-continued

Reductive amination/amidation catalytic relay.

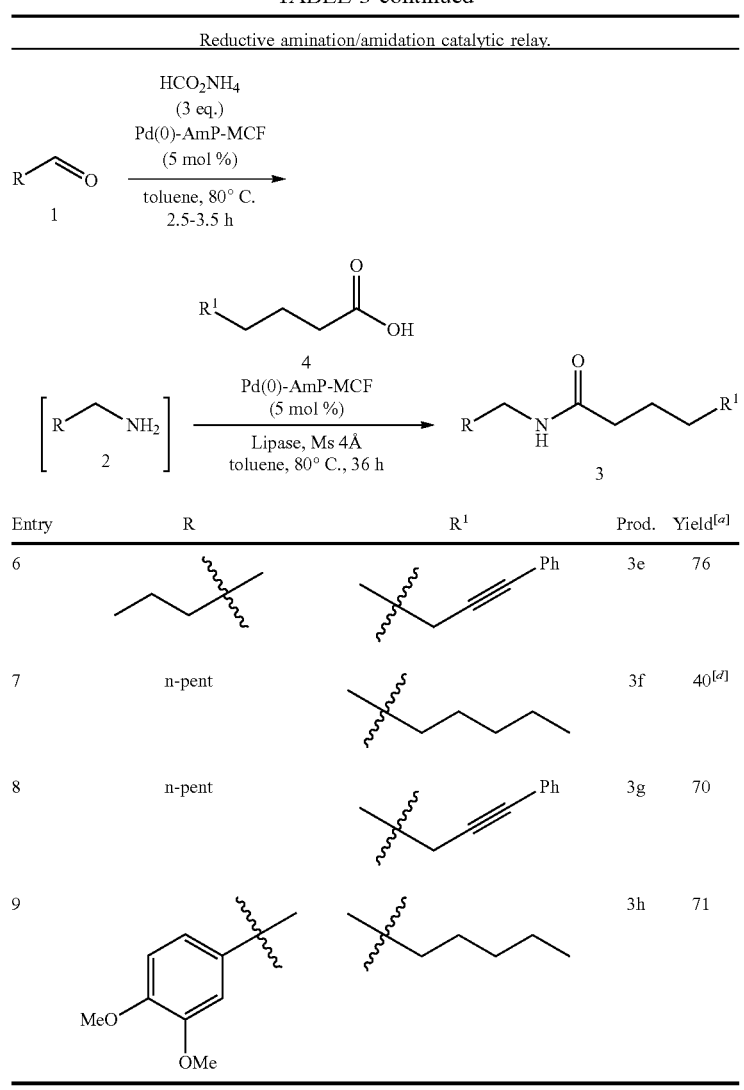

| Entry | R | R¹ | Prod. | Yield[a] |
|---|---|---|---|---|
| 6 | (sec-butyl branched alkyl) | —C≡C—Ph | 3e | 76 |
| 7 | n-pent | (branched alkyl) | 3f | 40[d] |
| 8 | n-pent | —C≡C—Ph | 3g | 70 |
| 9 | (3,4-dimethoxyphenyl ethyl, MeO/OMe) | (branched alkyl) | 3h | 71 |

[a]Isolated yield of pure product 6.
[b]Pd⁰-AmP-CPG (6.6 mol %) as catalyst.
[c]Starting acid 4b (Z:E = 85:15).
[d]100% conv. to 2d and 3f (50:50 ratio).

The co-catalytic one-pot total syntheses were highly chemoselective and gave the corresponding valuable 3b and 3c after one-step purification in 73 and 78% overall yield, respectively. Moreover, the synergistically heterogeneous Pd and lipase-catalyzed in situ amidation step tolerated aromatic, heterocyclic and aliphatic substituents with respect to the aldehyde component as well as functional acids to give 3a-3d mostly in good to high overall yields (two in situ steps). Here, a clear substrate specificity of CALB with respect towards both the in situ generated amine substrate and the amide donor was observed. For example, acid 4a was a better donor for the intermediate vanillyl amine 2a as compared to n-hexyl amine 2d (entries 1 and 7). The long-chain alkyne functionalized fatty acid 4b turned out to be a very good donor for the enzyme. Performing the co-catalytic one-pot reductive amination/amidation cascade reaction at a 0.5 g scale of 1a provided 3a in good yield (51%, 0.5 g).

General Procedure for Reductive Amination/Amidation Catalytic Relay.

A microwave-vial containing a solution of 1 (0.2 mmol, 1.0 equiv.), ammonium formate (37.8 mg, 0.6 mmol, 3.0 equiv.) and Pd⁰-catalyst (Pd⁰-AmP-MFC, 13.4 mg, 0.01 mmol, 8 wt %, 5 mol %) or (Pd⁰-CPG, 569 Å, 74.0 mg, 0.013 mmol, 6.6 mol %) in toluene (1 mL) under N₂ conditions was stirred at 80° C. for the time shown in Table 3. Afterwards, molecular sieves 4 Å, acid 4 (0.2 mmol, 1.0 equiv.) and lipase (120 mg/mmol) were added to reaction mixture and stirred at 80° C. for 36 h. The crude reaction mature was filtrated through Celite using CHCl₃ (10 mL) as eluent and evaporated. The crude material was purified by silica gel flash column chromatography to afford the corresponding amide 3 as indicated in Table 3. The lipase is preferably Novozyme-435 immobilized on a macroporous anionic resin.

Large Scale General Procedure:

A flask containing a solution of 1a (500 mg, 3.28 mmol, 1.0 equiv.), ammonium formate (620 mg, 9.84 mmol, 3.0 equiv.) and Pd⁰-AmP-MCF catalyst (219.7 mg, 0.16 mmol, 8 wt %, 5 mol %) in toluene (16.4 mL) under N₂ conditions was stirred at 80° C. for 3 h. Afterwards, molecular sieves 4 Å, acid 4 (3.28 mmol, 1.0 equiv.) and lipase (120 mg/mmol) were added to reaction mixture and stirred at 80° C. for 40 h. The crude reaction mixture was filtrated through Celite using CHCl₃ (10 mL) as eluent and evaporated. The crude material was purified by silica gel flash column chromatography. The final product 3a was isolated in 51% yield (491 mg, 1.7 mmol).

Example 4—Aerobic Oxidation/Reductive Amination/Amidation Catalytic Relay

A co-catalytic aerobic oxidation/reductive amination/amidation sequence starting from an alcohol substrate 5a was also developed as indicated in Scheme 7. Notably, alcohol 5a was converted to nonivamide 3a in one-pot (49% yield) using a multi-catalyst system.

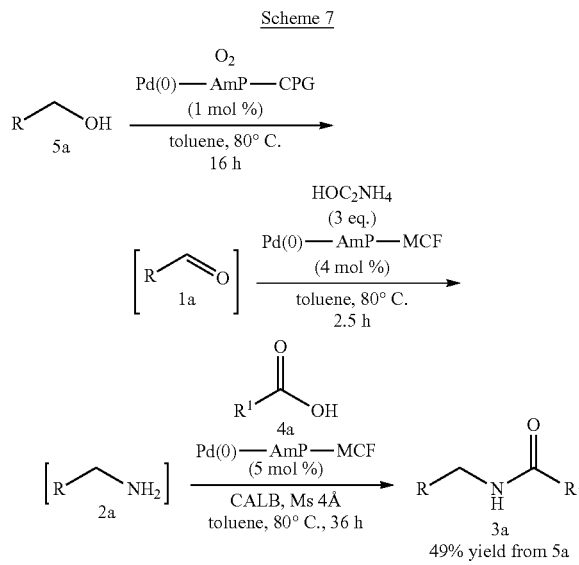

General Procedure for Aerobic Oxidation/Reductive Amination/Amidation Catalytic Relay To a microwave-vial containing a solution of alcohol 5a (0.2 mmol, 1.0 equiv.) and Pd⁰-AmP-CPG (10.1 mg, 0.002 mmol, 1 mol %) in dry toluene (0.25 mL) was connected a O₂ balloon. After stirring the reaction mixture for 16 h at 80° C., HCO₂NH₄ (37.8 mg, 0.6 mmol, 3.0 equiv.), Pd⁰-AmP-MFC (10.8 mg, 0.008 mmol, 8 wt %, 4 mol %) and toluene (0.75 mL) were added under N₂ conditions aid the reaction mixture was stirred at 80° C. for 2.5 h. Next, molecular sieves 4 Å, acid 4a (0.2 mmol, 1.0 equiv.) and lipase (120 mg/mmol) were added to the reaction mixture, which was stirred at 80° C. for 40 h. The crude reaction mixture was filtrated through Celite using CHCl₃ (10 mL) as eluent and next concentrated under reduced pressure. The crude material was purified by silica gel flash column chromatography.

Example 5—Synthesis of Amines from Ketones

A solution of Ketone (0.2 mmol, 1.0 equiv.) in CH₃OH (0.3 mL) was added to a microwave vial containing ammonium formate (126 mg, 2 mmol, 10.0 equiv.) and Pd⁰-Nanocatalyst (Pd⁰-AmP-MFC, 2.69 mg, 0.002 mmol, 8 wt %, 1 mol %) under N₂ conditions and stirred at 70° C. for 1-3 h. Next, the reaction mixture was cooled to room temperature and a saturated aqueous NaHCO₃ solution (0.3 mL) was added. The aqueous layer was extracted five times with CH₂Cl₂ (0.3×5 mL). The combined organic layers were dried over anhydrous Na₂SO₄ and concentrated under reduced pressure. The crude material was purified by silica gel flash column chromatography obtaining the corresponding amines.

Example 6—Catalytic Reductive Amination of Ketones

A heterogeneously Pd(0)-nanoparticle catalyzed reductive amination of ketones 1 with HCO₂NH₄ to give chiral primary amines was develop. The extensive condition screening revealed that the Pd⁰-Amp-MCF-catalyzed reductive amination of acetophenone 1m gave the corresponding alcohol 5m as the major product in toluene. The chemoselectivity switched to 2m when the transformation was performed in MeOH with a decreased and optimized catalyst loading (Table 4). Thus, the scope of the catalytic reductive amination of ketones 1 was investigated using this condition (Table 4).

TABLE 4

Ketone 1 substrate scope.

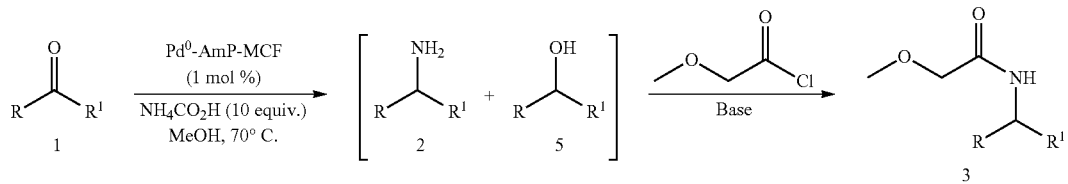

| Entry | Ketone | Amine | Ratio 2:5[a] | Time (h) | Conv. (%)[a] | Yield of 3 (%)[b] |
|---|---|---|---|---|---|---|
| 1 | 1m | 2m | 88:12 | 1.5 | >99 | 74 |

TABLE 4-continued
Ketone 1 substrate scope.
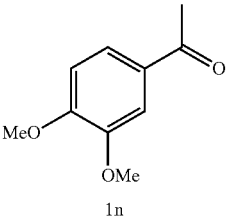
| Entry | Ketone | Amine | Ratio 2:5[a] | Time (h) | Conv. (%)[a] | Yield of 3 (%)[b] |
|---|---|---|---|---|---|---|
| 2 | 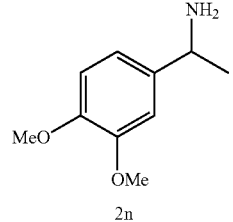 1n | 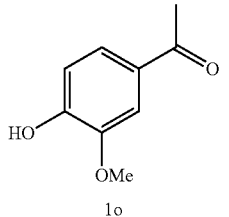 2n | 94:6 | 3 | 94 | 77 |
| 3 | 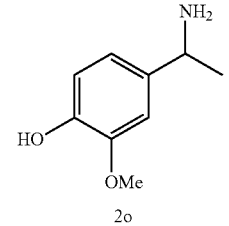 1o | 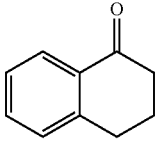 2o | 93:7 | 4.5 | 95 | 78 |
| 4 | 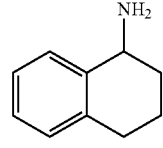 1p | 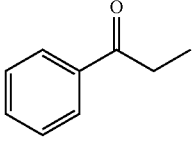 2p | 95:5 | 3.5 | 96 | 82 |
| 5 | 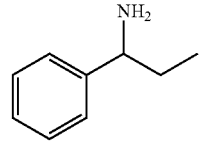 1q | 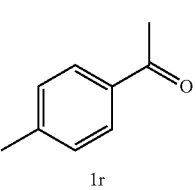 2q | 89:11 | 1.5 | >99 | 79 |
| 6 | 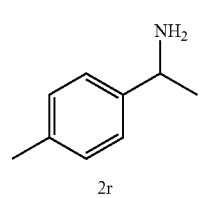 1r | 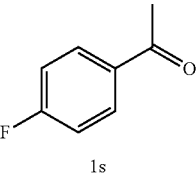 2r | 97:3 | 1.5 | >99 | 84 |
| 7 | 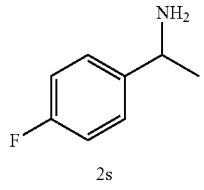 1s | 2s | 99:1 | 2.5 | 85 | 68 |

TABLE 4-continued

Ketone 1 substrate scope.

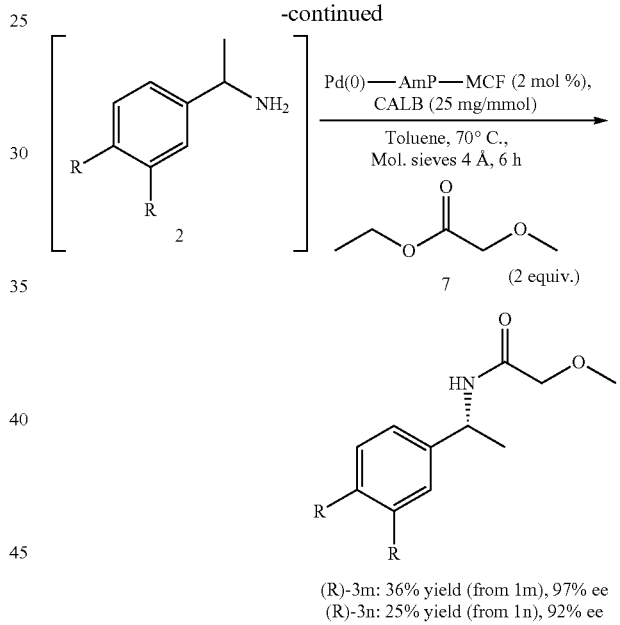

| Entry | Ketone | Amine | Ratio 2:5[a] | Time (h) | Conv. (%)[a] | Yield of 3 (%)[b] |
|---|---|---|---|---|---|---|
| 8 | 1t (cyclohexanone) | 2t (cyclohexylamine) | 99:1 | 3 | 93 | 75 |

[a]Determined by ¹HNMR analysis of the crude reaction mixture.
[b]Isolated yield of pure racemic 3.

The catalytic transformation exhibited high chemoselectivity and the corresponding racemic amides 3 were isolated in high yields after in situ amidation of amines 2.

General Procedure for Catalytic Reductive Amination of Ketones.

A vial containing a solution of 1 (0.2 mmol, 1.0 equiv.), $HCO_2NH_4$ (37.8 mg, 2 mmol, 10.0 equiv.) and $Pd^0$-nanocatalyst (Pd$^0$-AmP-MFC, 2.68 mg, 0.002 mmol, 8 wt %, 1 mol %) in MeOH (0.3 mL) under $N_2$ atmosphere was stirred at 70° C. for the time shown in table 4. Next, the solvent was evaporated and a solution of DIPEA (N,N-Diisopropylethylamine, 0.052 mL, 0.3 mmol, 1.5 equiv.) in dry dichloromethane (2.0 mL) followed by the addition of methoxy acetylchloride (0.4 mL, 0.51 mmol/mL, 1 equiv.) were added to the vial, which was flushed with Ar. After stirring overnight at room temperature, reaction mixture was filtered through Celite with $CH_2Cl_2$ (2.5 mL) and the solvent was removed under reduced pressure. The racemic α-methoxyacetamides 3 were next isolated by silica gel flash column chromatography.

Example 7—Reductive Amination/KR Catalytic Relay

With these results in Example 6 at hand, the heterogeneous metal/enzyme asymmetric relay catalysis strategy was tested. The heterogeneous metal/enzyme co-catalyzed reductive amination/kr relay sequence was first investigated (Scheme 8).

Scheme 8

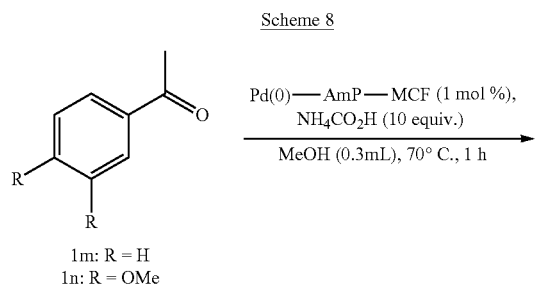

1m: R = H
1n: R = OMe

-continued (R)-3m: 36% yield (from 1m), 97% ee
(R)-3n: 25% yield (from 1n), 92% ee Here ester 7 was employed as the acyl donor since it has been previously been shown to improve the acylation rate of amines by hydrogen bond-activation in the active site of CALB. The use of Pd-nanoparticles in combination with CALB as co-catalysts for the dkr of secondary amines has recently been reported. Thus, we could also expect this type of process instead of kr in the presence of the Pd-catalyst. The catalytic relay sequence was performed in one-pot converting ketones 1m and 1n to the corresponding amides (R)-3m and (R)-3n in 36% and 25% overall isolated yield with 97 and 92% enantiomeric excess, respectively. While >76% of the ketone 1 m was converted to 2m, it was next converted in around 50% to amide (R)-3m by the co-catalytic amidation. Thus, the final transformation of the catalytic relay sequence had performed according to a kinetic resolution step. The presence of Pd$^0$-Amp-MCF catalyst was essential for the amidation to occur since also this time the Pd⁰-Amp-MCF had operated as a co-catalyst converting the excess formic acid to $H_2$, $CO_2$ and $H_2O$ as described vide supra.

General Procedure for Reductive Amination/KR Catalytic Relay.

A vial containing a solution of 1 (0.2 mmol, 1.0 equiv.), $HCO_2NH_4$ (37.8 mg, 2 mmol, 10.0 equiv.) and Pd⁰-nanocatalyst (Pd⁰-AmP-MFC, 2.68 mg, 0.002 mmol, 8 wt %, 1 mol %) in MeOH (0.3 mL) under $N_2$ atmosphere was stirred at 70° C. for the time shown in table 4. Next, the solvent was evaporated and Pd⁰-Pd⁰-AmP-MFC (5.4 mg, 0.008 mmol, 8 wt %, 2 mol %), Novozyme-435 (50 mg/mmol) and Mol. sieves (4 Å, 100 mg) were added to the vial with amine product. The vial was evacuated three times and refilled with $H_2$. Dry toluene (0.6 mL) was added to the vial and the mixture was heated 70° C. followed by addition of ethyl methoxyacetate (47 µL, 0.4 mmol) and stirred for 6 h. Next, the crude reaction mixture was filtrated through Celite using $CHCl_3$ (10 mL) as eluent and evaporated. The crude material was purified by silica gel flash column chromatography.

Example 8—Reductive Amination/DKR Catalytic Relay

With these results in Example 7 at hand, a heterogeneous metal/enzyme co-catalyzed reductive amination/dkr relay sequence was developed (Scheme 9). It is known from the literature that the addition of $H_2$ gas can promote the racemization of amines 2 during a dynamic kinetic resolution step. We therefore increased the Pd catalyst loading as well as added $H_2$ after the catalytic reductive amination to 2 had been completed (Scheme 9). The co-catalytic reaction sequences assembled the corresponding amides (R)-3 in good overall yields with high enantiomeric excess from ketones 1.

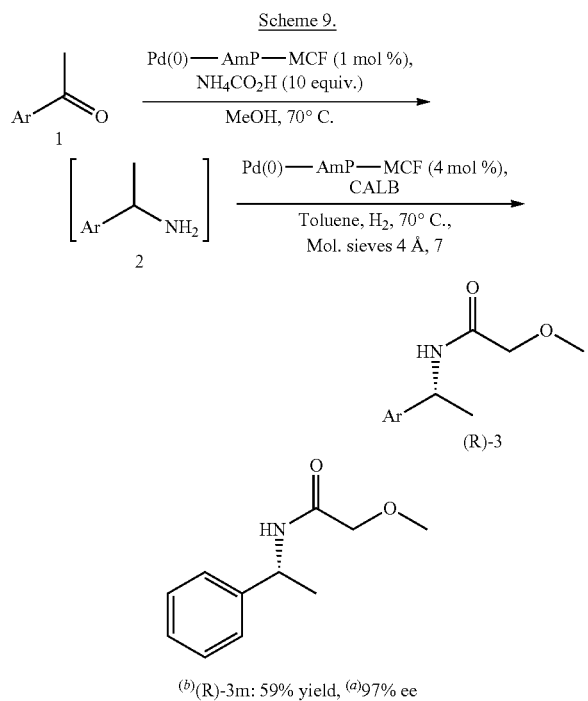

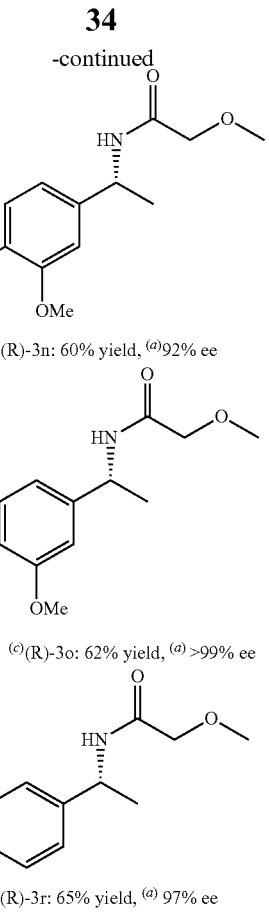

(a) Isolated overall yield from 1. (b) 12 h. (c) $Na_2CO_3$ instead of Mol sieve (4Å). 20 h. (d) 16 h.

Reductive Amination/DKR Catalytic Relay.

A vial containing a solution of 1 (0.2 mmol, 1.0 equiv.), $HCO_2NH_4$ (37.8 mg, 2 mmol, 10.0 equiv.) and Pd⁰-nanocatalyst (Pd⁰-AmP-MFC, 2.68 mg, 0.002 mmol, 8 wt %, 1 mol %) in MeOH (0.3 mL) under $N_2$ atmosphere was stirred at 70° C. for the time shown in table 4. Next, the solvent was evaporated and Pd⁰-Nanocatalyst (Pd⁰-AmP-MFC, 10.72 mg, 0.008 mmol, 8 wt %, 4 mol %), Novozyme-435 (50 mg/mmol) and additive (mol. siev. 4 Å (100 mg) or dry $Na_2CO_3$ (20 mg)] were added to the vial with amine product. The vial was evacuated three times and refilled with $H_2$. Dry toluene (0.6 mL) was added to the vial, and a balloon containing $H_2$ was connected to the vial. The mixture was heated 70° C. followed by addition of ethyl methoxyacetate (47 µL, 0.4 mmol) and stirred for the time shown in the Scheme. Next, the crude reaction mixture was filtrated through Celite using $CHCl_3$ (10 mL) as eluent and evaporated. The crude material was purified by silica gel flash column chromatography.

Example 9—Reductive Amination/KR Catalytic Relay

A heterogeneous metal/enzyme co-catalyzed reductive amination/kinetic resolution relay sequence using a combination of Pd⁰-Amp-MCF and transaminase (ATA, EC 2.6.1.18) as catalysts was also developed (Scheme 10). The one-pot catalytic relay sequence was successful and the corresponding amines (S)-2 or (R)-2 were assembled from ketones 1 and ammonium formate with high enantiomeric excess, respectively.

Scheme 10.

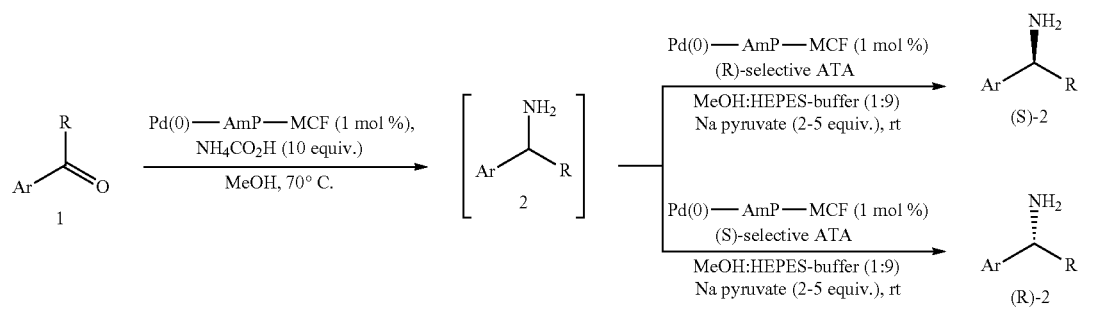

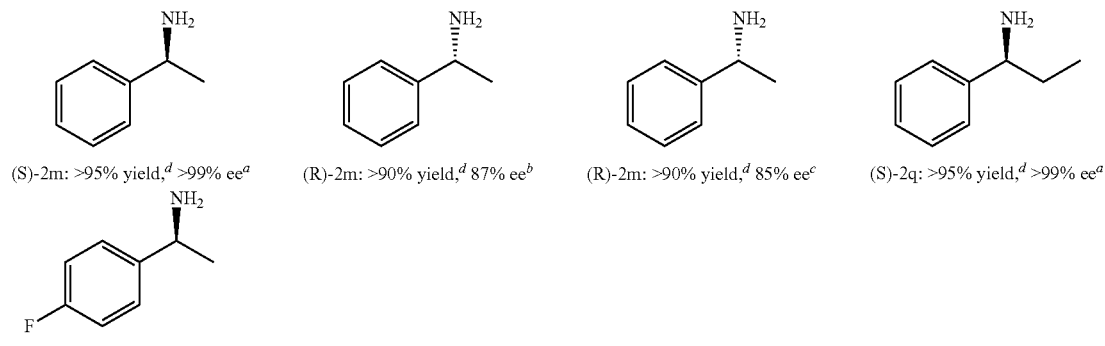

(a) ATA-117 was employed. (b) ATA-113 was employed. (c) Chromobacterium violacum (CV-ATA) was employed. d) Yield based on reacted ketone based on chiral-phase HPLC analysis. HEPES (50 mM) solution was used.

Reductive Amination/KR Catalytic Relay.

A vial containing a solution of 1 (0.2 mmol, 1.0 equiv.), $HCO_2NH_4$ (37.8 mg, 2 mmol, 10.0 equiv.) and $Pd^0$-nanocatalyst ($Pd^0$-AmP-MFC, 2.68 mg, 0.002 mmol, 8 wt %, 1 mol %) in MeOH (0.3 mL) under $N_2$ atmosphere was stirred at 70° C. for the time shown in table 4. Next, the vial was put on ice and methanol (0.367 mL) was added, followed by 6 mL of an aqueous buffer solution (50 mM HEPES, pH 8.2) containing amine transaminase (ATA) and 2-5 equivalents sodium pyruvate (1 equiv.=0.2 mmol, 22 mg). The tubes were put in darkness and room temperature for 24 hours with gentle mixing on an orbital shaker. Enantiomeric excess (ee) was determined by HPLC analysis (triplicate samples).

Example 10—Procedure for the Recycling of the Pd Nanoparticles (Tables 5-7)

A microwave-vial containing a solution of 1d or 1a (0.2 mmol, 1.0 equiv.), ammonium formate (37.8 mg, 0.6 mmol, 3.0 equiv.) and $Pd^0$-catalyst ($Pd^0$-CPG, 569 Å, 74.0 mg, 0.013 mmol, 6.6 mol %) in toluene was stirred at 80° C. Next, the reaction mixture was transferred to a centrifuge-vial and $CH_2Cl_2$ (8 mL) was added and after centrifugation, the supernatant liquid was removed and the catalyst washed with $CH_2Cl_2$ (8 mL) 3 times. Afterwards the catalyst was dried under vacuum.

TABLE 5

Recycling studies of $Pd^0$-AmP-CPG for the synthesis 2d.

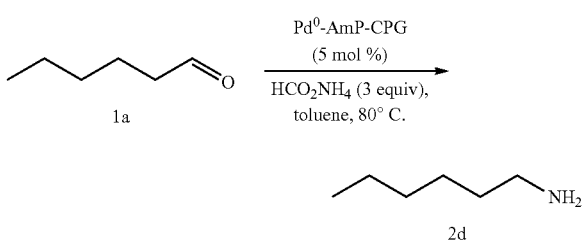

| Cycle | Time (h) | Conv. to 2d (%)[a] |
|---|---|---|
| 1 | 3.5 | 93 |
|   |     | (87% yield)[b] |
| 2 | 3.5 | 93 |
| 3 | 3.5 | 92 |
| 4 | 3.5 | 93 |
| 5 | 3.5 | 92 |
| 6 | 3.5 | 90 |

[a]Determined by $^1$H NMR analysis of the crude reaction mixture.
[b]Isolated yield of pure compound after silica gel column chromatography.

TABLE 6

Recycling studies of Pd⁰-AmP-MCF for the synthesis 2d.

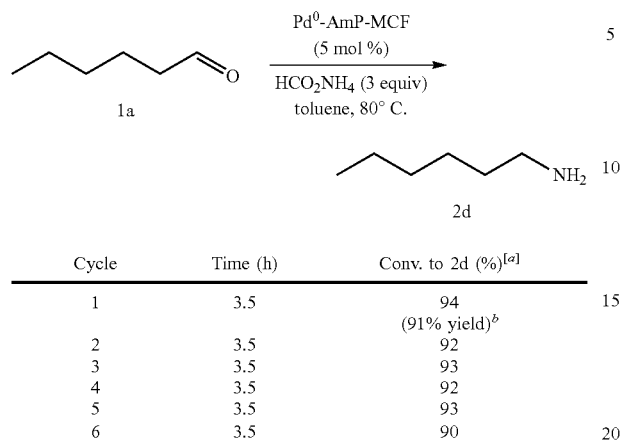

| Cycle | Time (h) | Conv. to 2d (%)[a] |
|---|---|---|
| 1 | 3.5 | 94 (91% yield)[b] |
| 2 | 3.5 | 92 |
| 3 | 3.5 | 93 |
| 4 | 3.5 | 92 |
| 5 | 3.5 | 93 |
| 6 | 3.5 | 90 |

[a]Determined by 1H NMR analysis of the crude reaction mixture.
[b]Isolated yield of pure compound after silica gel column chromatography.

TABLE 7

Recycling studies of Pd⁰-AmP-CPG for the synthesis of 2a.

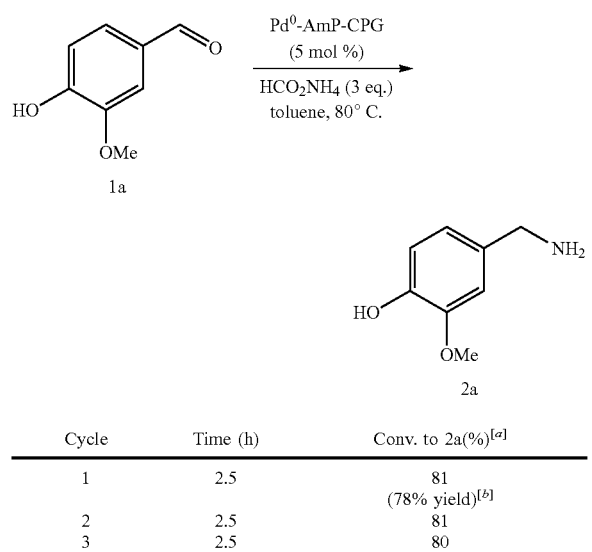

| Cycle | Time (h) | Conv. to 2a(%)[a] |
|---|---|---|
| 1 | 2.5 | 81 (78% yield)[b] |
| 2 | 2.5 | 81 |
| 3 | 2.5 | 80 |
| 4 | 2.5 | 80 |
| 5 | 2.5 | 80 |
| 6 | 2.5 | 80 |

[a]Determined by ¹H NMR analysis of the crude reaction mixture.
[b]Isolated yield of pure compound after silica gel column chromatography.

Example 11—HRMS Analysis the Reaction Mixture (Intermediate)

General Procedure:

The reaction was performed either between 1a and 2a. After stirring at 80° C. for 20 min., an aliquot (20 μL) was removed from the reaction mixture using a syringe and dissolved in 1.0 mL of a mixture of $CH_3CN/H_2O$ (70/30, v/v) and directly analysed by HRMS. LC-HRMS condition: ZORBX Eclipse Plus C18, 2.1×100 mm, 1.8-Micro column, Mobile Phase: $CH_3CN/H_2O$ (70/30, v/v), 0.3 mL/min, 230 nm. MS: Dual ESI ion source, positive mode, 65 eV. The intermediate I was confirmed by the HRMS analyses.

Scheme 11

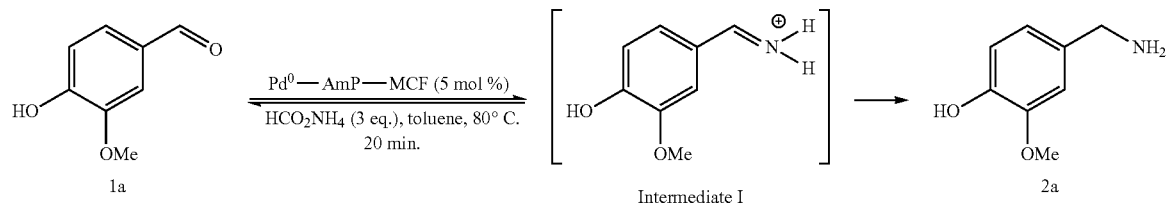

REFERENCES

[1] a) P. N. Rylander, Hydrogenation Methods, Academic Press, New York, 1985, 82. b) S. Gomez, J. A. Peters, T. Maschmeyer, *Adv. Synth. Catal.* 2002, 344, 1037. c) V. A. Tarasevich, N. G. Kozlov, *Russ. Chem. Rev.* 1999, 68, 55. d) W. S. Emerson, *Org. React.* 1948, 4, 174.

[2] L. Sung-Chan, B. P. Seung, *Chem. Commun.* 2007, 3714.

[3] Recent reviews: a) S. Gomez, J. A. Peters, T. Maschmeyer, *Adv. Synth. Catal.* 2002, 344, 1037. b) V. I. Tararov, A. Börner, *Synlett* 2005, 203. c) A. F. Abdel-Magid, S. J. Mehrman, *Org. Process Res. Dev.* 2006, 10, 971. d) T. C. Nugent, M. El-Shazly, *Adv. Synth. Catal.* 2010, 352, 753.

[4] a) R. P. Tripathi, S. S. Verma, J. Pandey, V. K. Tiwari, *Curr. Org. Chem.* 2008, 12, 1093; b) K. S. Hayes, *Appl. Catal.* 2001, 221, 187; c) T. S. Zatsepin, D. A. Stetsenko, M. J. Gait, T. S. Oretskaya, *Bioconjugate Chem.* 2005, 16, 471; d) J. M. Antos, M. B. Francis, *Curr. Opin. Chem. Biol.* 2006, 10, 253.

[5] a) R. Leuckart, Ber. Dtsch. *Chem. Ges.* 1885, 18, 2341; b) O. Wallach, Ber. Dtsch. Chem. Ges, 1891, 24, 3992; (c) C. B. Pollard, D. C. Young, *J. Org. Chem.* 1951, 16, 661. d) V. J. Webers, W. F. Bruce, *J. Am. Chem. Soc.* 1948, 70, 1422. e) M. L. Moore, The Leuckart Reaction, In *Organic Reactions*, Vol. 5, Ed. R. Adams, John Wiley and Sons, New York, 301. (1949).

[6] a) M. Kitamura, D. Lee, S. Hayashi, S. Tanaka, M. Yoshimura, *J. Org. Chem,* 2002, 67, 8687. b) C. Wang, A. Pettman, J. Bacsa, J. Xiao, *Angew. Chem. Int. Ed.* 2010, 49, 7548. c) R. Kadyrov, H. Riermeier, *Angew. Chem. Int. Ed.* 2003, 44, 5472.

[7] a) S. Ram, L. D. Spicer, *Tetrahedron Lett.* 1998, 29, 3741. b) R. W. Hanson, *J. Chem. Ed.* 1997, 74, 430.

[8] a) L. Yin, J. Liebscher, *Chem. Rev.* 2007, 107, 133; b) E. W. Ping, R. Wallace, J. Pierson, T. F. Fuller, C. W. Jones, *Microporous Mesoporous Mater.* 2010, 132, 174; c) M. Shakeri, C.-W. Tai, E. Göthelid, S. Oscarsson, J. E. Bäckvall, *Chem. Eur. J.* 2011, 17, 13269; d) E. V. Johnston, O. Verho, M. D. Kärkäs, M. Shakeri, C.-W. Tai, P. Palmgren, K. Eriksson, S. Oscarsson, J.-E. Bäckvall, *Chem. Eur. J.* 2012, 18, 12202; e) W. Long, N. A. Brunelli, S. A. Didas, E. W. Ping, C. W. Jones, *ACS Catal.* 2013, 3, 1700; f) K. Engström, E. V. Johnston, O. Verho, K. P. J. Gustafson, M. Shakeri, C.-W. Tai, J. E. Bäckvall, *Angew. Chem.* 2013, 125, 14256. g) O. Verho, A. Nagendiran, E. V. Johnston, C. W. Tai, J.-E. Bäckvall, *ChemCatChem* 2013, 5, 612. h) K. P. J. Gustafson, R. Lihammar, O. Verho, K. Engström, J-E. Bäckvall, *J. Org. Chem.* 2014, 79, 3747. i) O. Verho, K. P. Gustafson, A. Nagendiran, C.-W. Tai, *ChemCatChem* 2014, Early view. j) D. B. Bagal, R. A. Wattle, M. V. Khedkar, K. P. Dhake, B. M. Bhanage, *Catal. Sci. Technol.* 2012, 2, 354.

[9] a) L. Deiana, S. Afewerki, C. Palo-Nieto, O. Verho, E. V. Johnston, A. Córdova, *Sci. Rep.* 2012, 2, 851. b) L. Deiana, L. Ghisu, O. Córdova, S. Afewerki, R. Zhang, A. Córdova, Synthesis 2014, 1303. c) L. Deiana, L. Ghisu, S. Afewerki, O. Verho, E. V. Johnston, N. Hedin, Z. Bacsik, A. Córdova, *Adv. Synth. Catal.* 2014, 356, 2485. d) G. Ma, S. Afewerki, L. Deiana, C. Palo-Nieto, L. Liu, J. Sun, I. Ibrahem, A. Córdova, *Angew. Chem.* 2013, 52, 6050.

[10] a) *Multicomponent Reactions*. Eds J. Zhu, H. Bienayme, WILEY-VCH, Weinheim, 2005. b) R. C. Cioc, E. Ruijer, R. V. A. Orru, *Green. Chem.* 2014, 16, 2958.

[11] a) A. Leyva-Perez, P. Garcia-Garcia, A. Corma, *Angew. Chem.* 2014, 53, 8687. b) M. Anderson, S. Afewerki, P. Berglund, A. Córdova, *Adv. Synth. Catal,* 2014, 356, 2113. b) L. Deiana, Y. Jiang, C. Palo-Nieto, S. Afewerki, C. Incerti-Pradillos, O. Verho, C-W. Tai, E. V. Johnston, A. Córdova, *Angew. Chem.* 2014, 53, 3447;

[12] a) M. J. Caterina, M. A. Schumacher, M. Tominaga, T. A. Rosen, J. D. Levine, D. Julius, *Nature* 1997, 389 816. b) M. J. Caterina, T. A. Rosen, M. Tominaga, S. J. Brake, D. Julius, *Nature* 1999, 398, 436. c) D. Julius, A. I. Basbaum, *Nature* 2001, 413, 203. d) V. S. Govindarajan, M. N. Sathyanarayana, *Crit. Rev. Food Sci. Nutr.* 1991, 29, 435. e) T. Suzuki, K. Iwai, In *The Alkaloids*; Brossi, A., Ed.; Academic: New York, N.Y., 1984, 23, Chapter 4. f) R. Sancho, C. Lucena, A. Macho, M. A. Calzado, M. Blanco-Molina, A. Minassi, G. Appendino, E. Munoz, *Eur. J. Immunol.* 2002, 32, 1753. g) A. Morita, Y. Iwasaki, K. Kobata, T. Iida, T. Higashi, K. Oda, A. Suzuki, M. Narukawa, S. Sasakuma, H. Yokogoshi, S. Yazawa, M. Tominaga, T. Watanabe, *Life Sci.* 2006, 79, 2303.

The invention claimed is:

1. A method for conversion of an aldehyde or ketone comprising the steps of:
   Providing an aldehyde or a ketone,
   Converting the aldehyde or ketone to an amine, wherein the conversion to amine is catalyzed by a heterogeneous metal catalyst and the heterogeneous palladium catalyst is selected from Pd0-AmP-MCF (palladium (0)-aminopropyl-mesocellular foam) and Pd0-AmP-CPG (palladium(0)-aminopropyl-controlled pore glass),
   Converting the amine to an amide, wherein the conversion to amide is catalyzed by a heterogeneous metal catalyst.

2. The method according to claim 1, wherein the step of converting the aldehyde or ketone to an amine is catalyzed by the heterogeneous metal catalyst in the presence of ammonium formate ($HCO_2NH_4$) acting as an amine donor and reducing agent.

3. The method according to claim 1, wherein the step of converting the aldehyde or ketone to an amine is carried out at a temperature 22-100° C., wherein an organic solution is used as a solvent.

4. The method according to claim 1, wherein
   the step of converting the aldehyde or ketone to an amine is catalyzed by $Pd^0$-AmP-MCF (palladium(0)-aminopropyl-mesocellular foam) or $Pd^0$-AmP-CPG (palladium(0)-aminopropyl-controlled pore glass),
   the step of converting the amine to an amide is catalyzed by $Pd^0$-AmP-MCF and enzyme in the presence of acyl donor.

5. The method according to claim 1, wherein an enzyme is selected from the group consisting of lipase and amine transaminase (ATA).

6. The method according to claim 1, wherein
   the step of converting the aldehyde or ketone to an amine comprises the steps of mixing a ketone or aldehyde with ammonium formate and $Pd^0$-AmP-MCF or $Pd^0$-AmP-CPG in toluene, and subsequently stirring at a temperature of 22-100° C. for at least 1 hour, and wherein the reaction is carried for at least 1 hour,
   the step of converting the amine to an amide comprises the steps of:
   adding lipase B,
   adding an acyl donor, and
   mixing at a temperature of at least 22-100 C.° for at least 1 hour.

7. The method according to claim 6, wherein the aldehyde or ketone is an aldehyde of structural formula

wherein R is selected from one of the following substituents:

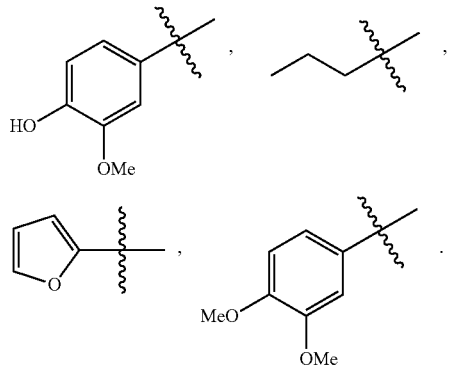

8. The method according to claim 6, wherein the acyl donor is an acid of structural formula

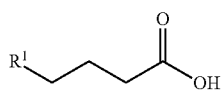

wherein $R^1$ is selected from one of the following substituents:

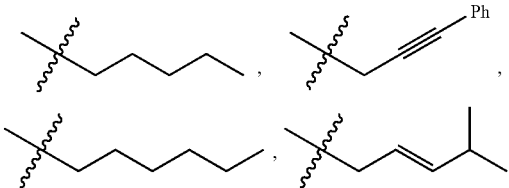

9. The method according to claim 6, wherein the resulting product is novinamide, capsaicin or phenylcapsaicin having the following respective structural formula:

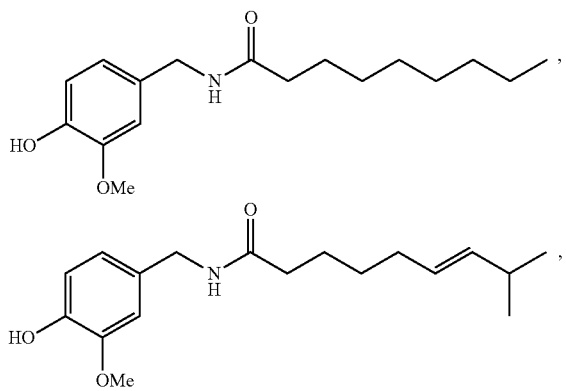

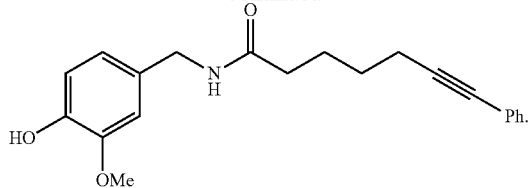

10. The method according to claim 1, wherein the step of converting the aldehyde or ketone to an amine comprises the steps of mixing a ketone or aldehyde with ammonium formate and Pd⁰-AmP-MCF in methanol, and subsequently stirring at a temperature of 22-100° C. for at least 1 hour, and wherein the reaction is carried for at least 1 hour, the step of converting the amine to an amide comprises the steps of:

evaporating the solvent, adding Pd⁰-AmP-MCF (palladium(0)-aminopropyl-mesocellular foam), adding CALB (*Candida Antarctica* lipase B), adding toluene under $H_2$ atmosphere, adding an acyl donor under $H_2$ atmosphere, and mixing under $H_2$ atmosphere for at least 1 hour.

11. The method according to claim 1, wherein the aldehyde or ketone is a ketone of structural formula

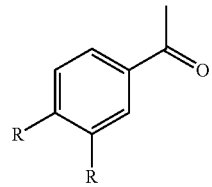

wherein R is selected from the group consisting of H, alkoxy and alkyl, and wherein the resulting amide is of structural formula

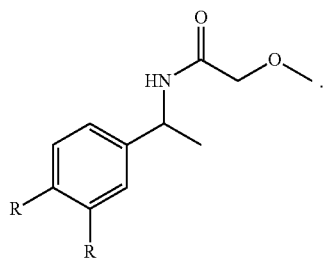

12. The method according to claim 11, wherein each R is selected from the group consisting of H, methoxy and methyl, and wherein the resulting amide is selected from the following amides:

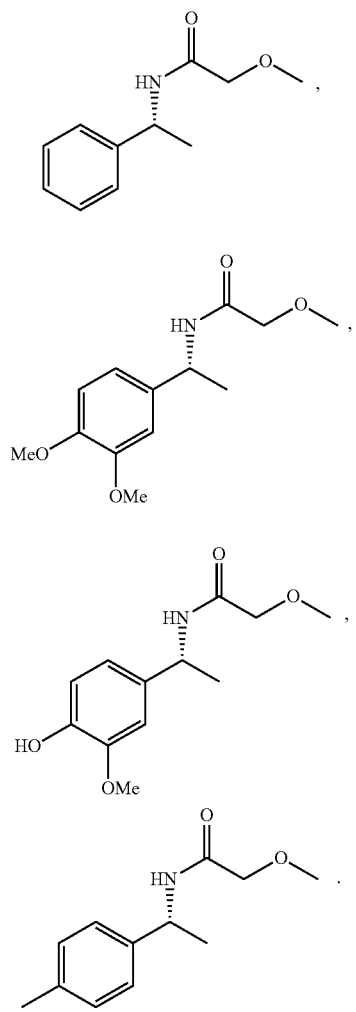

13. The method according to claim 1,
the step of converting the ketone to an amine comprises the steps of mixing a ketone with ammonium formate and Pd⁰-AmP-MCF in methanol, and subsequently stirring at a temperature of 22-100° C. for at least 1 hour, and wherein the reaction is carried for at least 1 hour, the step of converting the amine to an amide comprises the steps of:
evaporating the solvent,
adding DIPEA (N,N-Diisopropylethyamine),
adding dichloromethane,
adding methoxy acetylchloride, and
mixing for at least 1 hour.

14. The method according to claim 13, wherein the ketone is of structural formula

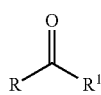

selected from:

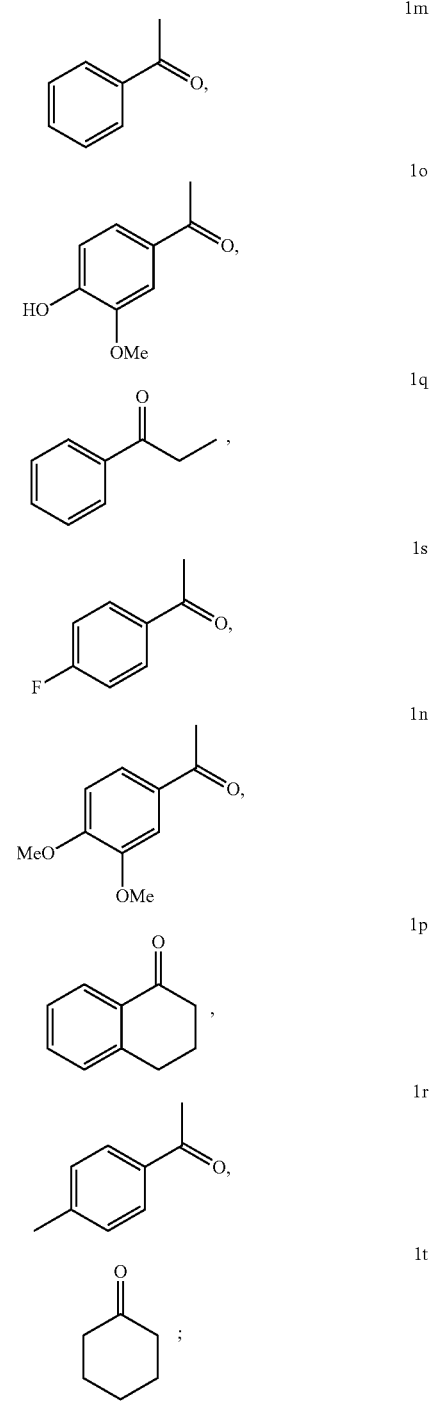

wherein the corresponding resulting amine in the amination step is of structural formula

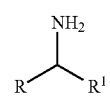

selected from:

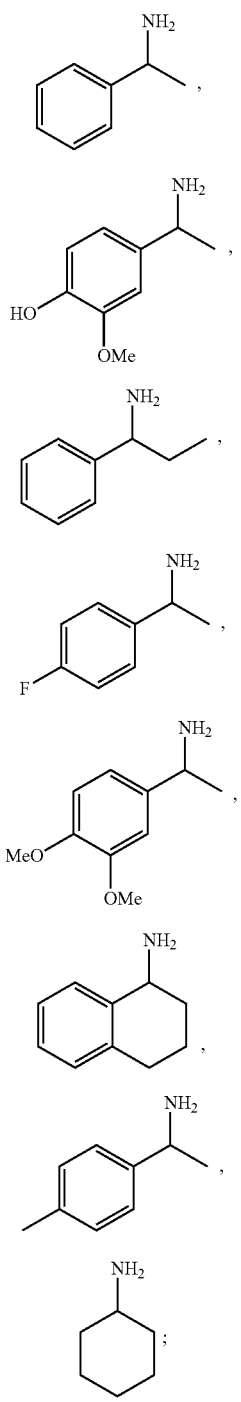

wherein the amino group of the above amine is in the amidation step acylated with a methoxyacetyl group and thereby the resulting amide in the amidation step is of formula

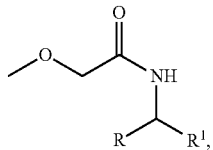

wherein R and $R^1$ is each selected from the group consisting of H, alkoxy, and alkyl.

15. The method according to claim 1, wherein
the step of converting the aldehyde or ketone to an amine comprises the steps of mixing a ketone or aldehyde with ammonium formate and $Pd^0$-AmP-MCF in methanol, and subsequently stirring at a temperature of 22-100° C. for at least 1 hour, and wherein the reaction is carried for at least 1 hour,
the step of converting the amine to an amide comprises the steps of:
putting the mixture on ice,
adding methanol to the mixture,
adding amine transaminase (ATA) and acyl donor,
mixing for at least 1 hour.

16. The method according to claim 1, wherein said conversion is performed in one pot without any purification of intermediates.

17. The method according to claim 1, wherein the aldehyde or ketone is provided by reacting an alcohol with $Pd^0$-AmP-CPG in the presence of $O_2$, wherein said alcohol is selected from the group consisting of primary alcohol, secondary alcohol and aldol.

18. A method for conversion of an aldehyde or ketone comprising the steps of:
Providing an aldehyde or a ketone,
Converting the aldehyde or ketone to an amine, wherein the conversion to amine is catalyzed by a heterogeneous metal catalyst and the heterogeneous palladium catalyst is selected from Pd0-AmP-MCF (palladium(0)-aminopropyl-mesocellular foam) and Pd0-AmP-CPG (palladium(0)-aminopropyl-controlled pore glass).

19. The method according to claim 18, wherein
the step of converting the aldehyde or ketone to an amine comprises the steps of mixing a ketone or aldehyde with ammonium formate and $Pd^0$-AmP-MCF (palladium(0)-aminopropyl-mesocellular foam) or $Pd^0$-AmP-CPG (palladium(0)-aminopropyl-controlled pore glass) in toluene or methanol, and subsequently stirring at a temperature of 22-100° C. for at least 1 hour, and wherein the reaction is carried for at least 1 hour.

* * * * *